United States Patent
Kelmartin, Jr. et al.

[11] Patent Number: 6,117,547
[45] Date of Patent: Sep. 12, 2000

[54] POLYTETRAFLUOROETHYLENE FIBER

[75] Inventors: Thomas Patrick Kelmartin, Jr., West Chester, Pa.; George M. Roberts, Havre de Grace, Md.; John W. Dolan, Boothwyn, Pa.; Raymond B. Minor, Elkton, Md.

[73] Assignee: Gore Enterprise Holdings, Inc., Newark, Del.

[21] Appl. No.: 09/404,434

[22] Filed: Sep. 23, 1999

Related U.S. Application Data

[62] Division of application No. 09/070,061, Apr. 30, 1998, Pat. No. 5,989,709.

[51] Int. Cl.$^7$ ........................................................ D01F 6/12
[52] U.S. Cl. ........................................... 428/364; 428/394
[58] Field of Search ..................................... 428/364, 394

[56] References Cited

U.S. PATENT DOCUMENTS

| | | | |
|---|---|---|---|
| 2,396,629 | 3/1946 | Alfthan et al. | 18/55 |
| 2,951,047 | 8/1960 | Lantos | 260/17 |
| 2,953,428 | 9/1960 | Hunt et al. | 18/54 |
| 3,953,566 | 4/1976 | Gore | 264/288 |
| 3,957,938 | 5/1976 | Gravley | 264/85 |
| 4,025,598 | 5/1977 | Sasshofer et al. | 264/140 |
| 4,064,214 | 12/1977 | FitzGerald | 264/147 |
| 4,069,291 | 1/1978 | Kidoh et al. | 264/342 R |
| 4,187,390 | 2/1980 | Gore | 174/102 R |
| 4,364,998 | 12/1982 | Wei | 428/399 |
| 4,505,982 | 3/1985 | Hoheisel | 428/421 |
| 4,510,300 | 4/1985 | Levy | 526/247 |
| 4,853,164 | 8/1989 | Kiang et al. | 264/22 |
| 5,004,648 | 4/1991 | Hane et al. | 428/364 |
| 5,061,561 | 10/1991 | Katayama | 428/364 |
| 5,167,890 | 12/1992 | Sasshofer et al. | 264/127 |
| 5,258,014 | 11/1993 | Harada et al. | 606/228 |
| 5,262,234 | 11/1993 | Minor et al. | 428/372 |
| 5,281,475 | 1/1994 | Hollenbaugh, Jr. et al. | 428/357 |
| 5,288,552 | 2/1994 | Hollenbaugh, Jr. et al. | 428/357 |
| 5,294,389 | 3/1994 | Hain et al. | 264/85 |
| 5,294,395 | 3/1994 | Broyer | 264/178 F |
| 5,364,699 | 11/1994 | Hollenbaugh, Jr. et al. | 428/357 |
| 5,460,882 | 10/1995 | Vita et al. | 428/364 |
| 5,470,655 | 11/1995 | Hirai | 428/364 |
| 5,552,219 | 9/1996 | Vita et al. | 478/357 |
| 5,562,986 | 10/1996 | Yamamoto et al. | 428/364 |
| 5,562,987 | 10/1996 | Shimizu | 428/364 |
| 5,573,639 | 11/1996 | Schmitz et al. | 162/140 |
| 5,591,526 | 1/1997 | Abrams et al. | 428/401 |
| 5,618,481 | 4/1997 | Vita et al. | 264/103 |
| 5,635,124 | 6/1997 | Abrams et al. | 264/257 |
| 5,686,033 | 11/1997 | Shimizu | 264/127 |
| 5,989,709 | 11/1999 | Kelmartin | 428/394 |

FOREIGN PATENT DOCUMENTS 59-224802  12/1984  Japan.

*Primary Examiner*—N. Edwards
*Attorney, Agent, or Firm*—Alan M. Wheatcraft

[57] ABSTRACT

A PTFE fiber that is adapted to be sewn at high speeds. The fiber has a toughness greater than about 0.36 grams per denier (g/d). A range for the toughness is from about 0.36 to about 1.01 g/d, with a preferred range being from about 0.50 to about 0.80 g/d. The toughness of the inventive PTFE fiber is most preferably about 0.60 g/d. The inventive fiber has a peak engineering stress greater than about 1.6 g/d and a break strain greater than about 15.5 percent. A preferred range for the peak engineering stress is from about 3.0 g/d to about 5.0 g/d, and a preferred range for the break strain is from about 20 percent to about 50 percent. Most preferably, the peak engineering stress is about 4.4 g/d, and the break strain is about 24 percent. In another aspect, this invention provides a process for making a fiber that involves providing a PTFE fiber and heating the PTFE fiber to a temperature of from about 300° C. to about 500° C., while overfeeding the PTFE fiber at an overfeed of up to about 70 percent. A preferred range for the temperature is from about 350° C. to about 450° C., and a preferred range for the overfeed in the overfeeding step is from about 10 percent to about 20 percent. Most preferably, the temperature in the heating step is about 400° C. and the overfeed in the overfeeding step is about 15 percent. The PTFE fiber may be used as a filament for an improved dental floss, and is also suited for an improved bearing material.

19 Claims, 33 Drawing Sheets

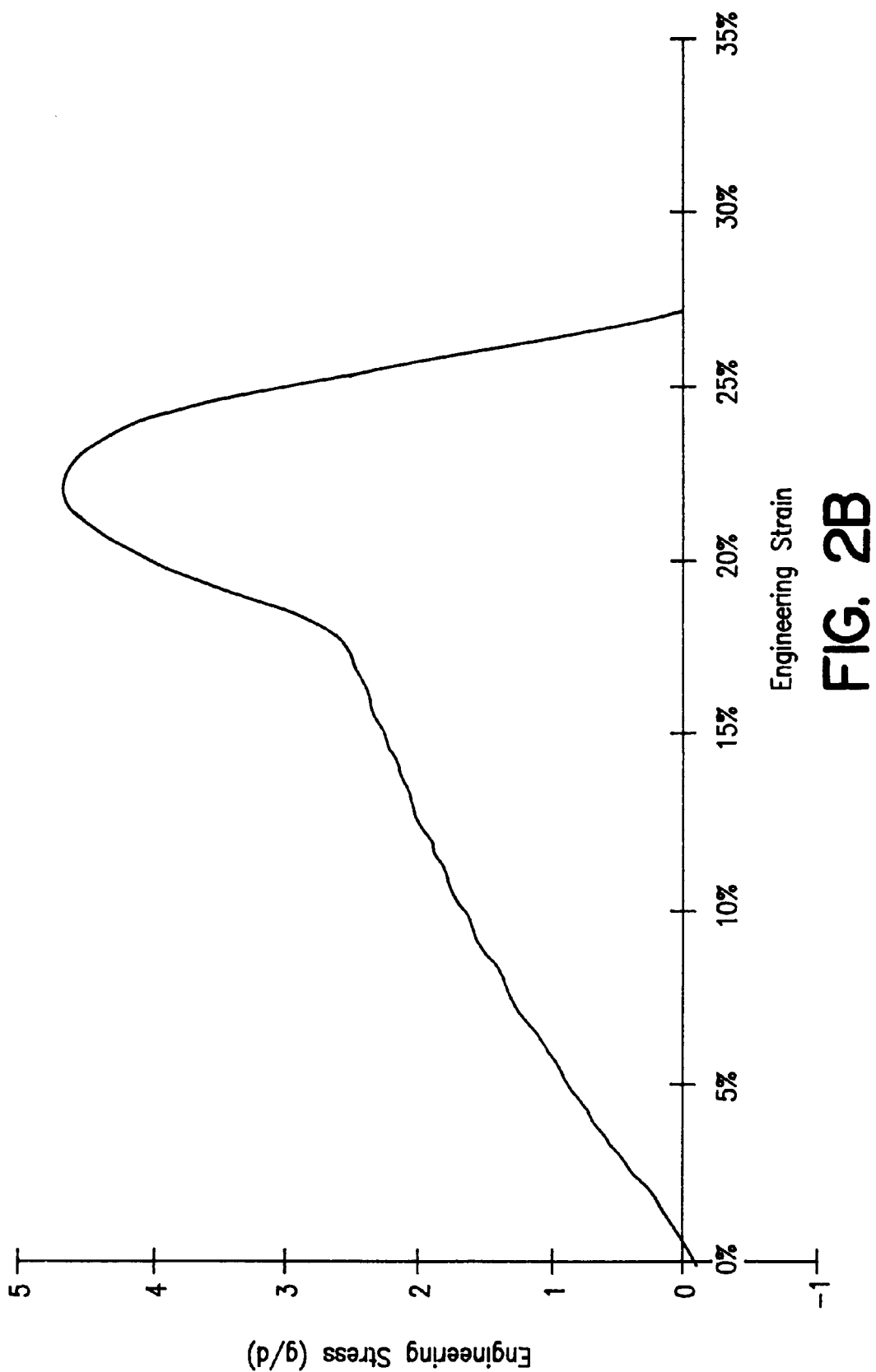

POLYTETRAFLUOROETHYLENE FIBER

RELATED APPLICATIONS

The present application is a divisional of U.S. patent application Ser. No. 09/070,061 filed Apr. 30, 1998, now U.S. Pat. No. 5,987,709.

FIELD OF THE INVENTION

This invention generally relates to polytetrafluoroethylene (PTFE) fiber, and more specifically, to a PTFE fiber with improved toughness.

BACKGROUND OF THE INVENTION

PTFE fiber is used in numerous demanding applications due to the robust physical properties of PTFE. It has excellent high and low temperature performance, chemical resistance, and resistance to damage as a result of exposure to solar ultraviolet radiation. Exemplary applications of PTFE fiber include use as a dental floss, a bearing, and fabric formed from a wide array of textile processes including weaving, braiding, knitting and needlepunching. PTFE fiber is also used as a sewing thread.

PTFE sewing thread is typically produced by forming or acquiring a PTFE fiber, twisting it longitudinally to obtain a pseudo-round cross section, and then exposing the twisted fiber to elevated temperatures in order to permanently set the twist in the fiber. PTFE fiber can be produced through various methods. These methods include multi-filament emulsion spinning (such as described in U.S. Pat. No. 2,772,444), paste extruding and expansion (such as described in U.S. Pat. No. 3,953,566), and paste extruding and melt-stretching (such as described in U.S. Pat. No. 5,167,890).

Sewing thread manufactured by any of the above methods is typically difficult to sew. Sewing thread made from emulsion-spun multi-filament PTFE, for example, is approximately one-half or less as strong as other PTFE sewing threads. As a result, thread breaks during sewing with emulsion spun PTFE are very common. This material is also only available in brown or white (bleached brown).

Sewing thread made from either of the paste extrusion methods, while stronger than emulsion-spun material, is also difficult to sew, particularly as compared to common polyester sewing thread. Care should be taken when setting-up a sewing machine to handle PTFE fiber. Of particular importance are thread tension adjustments, machine timing, thread lubrication and needle selection. Even when these steps are taken, breaking of PTFE sewing thread may occur. Breaks usually occur more frequently per linear distance as the sewing speed (stitches per minute) is increased.

Polyester sewing thread is robust in sewing due in part to the mechanical properties of the thread. In particular, the "toughness" (as defined herein) of the polyester thread appears to be much higher than that of typical PTFE threads.

The sewing process generates relatively high frequency (greater than about 1000 cycles per minute) tensile loading on the sewing thread. As the sewing speed is increased, the frequency of this loading correspondingly increases. As used herein with reference to sewing, "high speed" means 1500 stitches per minute or greater on a lockstitch sewing machine.

When the sewing thread is subject to tension during the sewing process, it reacts by both elastic and inelastic deformation (temporary and permanent stretching). Without being limited by theory, it is possible that the polyester sewing thread breaks much less often than PTFE sewing thread run under comparable conditions because of the higher level of toughness of the polyester. The increased toughness allows the polyester sewing thread to more readily absorb the tensile loading during sewing through stretching of the sewing thread.

A PTFE fiber having increased toughness is desirable in many applications. In particular, a PTFE fiber adapted to being sewn at high speed is desirable.

SUMMARY OF THE INVENTION

The present invention provides a PTFE fiber that has a toughness greater than about 0.36 grams per denier (g/d). A range for the toughness is from about 0.36 g/d to about 1.01 g/d, with a preferred range being from about 0.50 g/d to about 0.80 g/d. The toughness of the inventive PTFE fiber is most preferably about 0.60 g/d.

The inventive fiber has a peak engineering stress greater than about 1.6 g/d and a break strain greater than about 15.5 percent. A preferred peak engineering stress is greater than about 2.0 g/d, and a preferred break strain is greater than about 20 percent. More preferable is a peak engineering stress greater than about 2.5 g/d and a break strain greater than about 25 percent. Still more preferable is a peak engineering stress greater than about 3.0 g/d and a break strain greater than about 30 percent. A preferred range for the peak engineering stress is from about 3.0 to about 5.0 g/d, and a preferred range for the break strain is from about 20 to about 50 percent. Most preferably, the peak engineering stress is about 4.4 g/d, and the break strain is about 24 percent.

In another aspect, this invention provides a process for making a fiber that involves providing a PTFE fiber and heating the PTFE fiber to a temperature of from about 300° C. to about 500° C., while overfeeding the PTFE fiber at an overfeed of up to about 70 percent. A preferred range for the temperature is from about 350° C. to about 450° C., and a preferred range for the overfeed in the overfeeding step is from about 10 percent to about 20 percent. Most preferably, the temperature in the heating step is about 400° C. and the overfeed in the overfeeding step is about 15 percent.

In another aspect, this invention provides an improved emulsion-spun PTFE fiber which has a toughness greater than 0.18 g/d.

BRIEF DESCRIPTION OF THE DRAWINGS

FIG. 2B is a graph illustrating the properties of a polyester fiber.

DETAILED DESCRIPTION OF THE INVENTION

The fiber of this invention has properties derivable from a stress-strain diagram for the fiber. As used herein, "engineering strain" means the change in length of a test specimen divided by the original length of the specimen, and is normally expressed as a percent; "peak engineering stress" means the greatest load supported by the fiber (according to tests described herein) and is represented by the peak of the stress-stain curve for the fiber (expressed in grams per denier); "break strain" means the engineering strain after break where the engineering stress has returned to zero; "toughness" means the area under the stress-strain curve as measured from the point where strain equals zero to the break strain (the details of how the toughness is measured are described below); and "denier" means a unit of linear density expressed in grams per 9000 meters.

Figure 1:
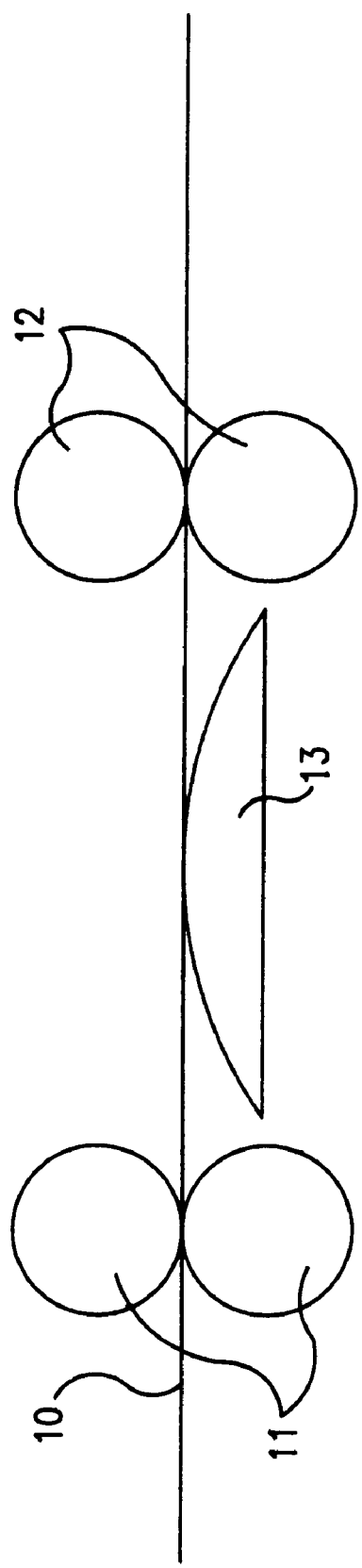
FIG. 1 is a schematic representation of an exemplary embodiment of the process according to this invention.

This invention provides a PTFE fiber that is capable of being sewn at high speed. This fiber is produced according to the method schematically represented in FIG. 1. A PTFE fiber 10, which can be any desired denier, is first manufactured or obtained. If manufactured, it is made according to conventional methods known in the art. The PTFE fiber 10 is then overfed at an overfeed rate of 5 to 70 percent over a heat source 13. The overfeeding may be accomplished by feeding fiber 10 through input nip rolls 11 to output nip rolls 12 as shown in FIG. 1. Rolls 11 are sized, or their speed is adjusted, such that they pay out a desired amount more of fiber 10 than is taken up by rolls 12. For example, a ten percent overfeed rate means that rolls 11 pay out fiber 10 over heat source 13 at a rate ten percent faster than fiber 10 is taken up by rolls 12. By overfeeding and simultaneously heating fiber 10 according to this process, fiber 10 shrinks in its linear direction, thus increasing its denier. Fiber 10 may be wound from rolls 12 onto cores and may be further handled in normal manufacturing processes such as spool winding or bobbin winding.

PTFE fiber 10 may alternatively be an expanded PTFE (ePTFE) fiber. Such ePTFE fiber may be produced according to the method disclosed in U.S. Pat. No. 3,953,566, which is incorporated herein for its teaching on ePTFE fiber production. When an ePTFE fiber is used, such fiber initially has a substantially white appearance (if not pigmented with color) before treatment according to this invention (i.e., before passing through nip rolls 11 in FIG. 1). After treatment according this invention (i.e., after passing through nip rolls 12 in FIG. 1), the fiber typically changes to a substantially translucent appearance. The translucent fiber is advantageous because it blends into colored fabric without having to be a color closely matching that of the fabric.

Fiber 10 may also be twisted before being subjected to the overfeeding and heating steps of this process. If twisted, the fiber may have, for example, seven turns per inch in the "z" or "s" direction. Untwisted fibers produced according to this invention have use in applications where the ability of the fiber to absorb tension fluctuations is important. Such applications include weaving, braiding, knitting, and needlepunching.

Heat source 13 may be a hot plate, heated godets, hot air, hot liquid ovens, radiant heating, or any other means adapted to heat the fiber while allowing it to shrink in a controlled fashion. The heat source may be operated at a temperature of from about 300° C. to about 500° C. A preferred range is about 350° C. to about 450° C., with a most preferred temperature being about 400° C.

Nip rolls 11 and 12 may alternatively be godets with fiber 10 wrapped around them, or any other fiber pay-off and take-up system as will be understood by those skilled in the art.

In an alternative embodiment of the process of this invention, an additional heat treatment of fiber 10 (after roll 12) may be included. This additional heat treatment step, which occurs after the simultaneous overfeeding and heating steps disclosed above, may also be performed at a temperature of from about 300° C. to about 500° C., preferably at 400° C. This alternative heat treatment should be done at zero percent overfeed such that no substantial expansion or contraction of the fiber occurs. The optional heating step is used to condition fiber 10 to prevent subsequent length changes during handling or end use.

As a further alternative, a sewing thread lubricant, such as a silicone oil compound, may be applied to the sewing thread in subsequent packaging operations (after roll 12 or the alternative heat setting step). The silicone oil is believed to reduce friction, and therefore temperature, at the sewing needle at high speed.

Fiber produced according to this invention has surprisingly improved properties, including peak engineering stress, break strain, toughness, and success on sewing machines at high speed ("sewability"). The inventive fiber has many applications in which the improved properties provide improved performance.

One such application is a sewing thread where the improved properties allow the fiber to be sewn at high speeds with fewer thread breaks than conventional PTFE fibers, along with other advantages. The inventive fiber may also be used to fabricate bearings, where the improved properties are expected to provide greater abrasion resistance, longer product life, and other advantages. To form bearings, the fiber may be towed according to techniques known in the art, or multi-filament fibers may be used, in which one or more of the inventive fibers are twisted together with themselves or with any other suitable natural or man-made fiber, such as polyester, polypropylene, or nylon (the multi-filament embodiment may also alternatively be used in other applications of the inventive fiber). Low denier fibers (less than 100 denier, for example) may be used in some bearing applications. Whether the inventive fiber is used as a monofilament, a multi-filament, or towed, it may be woven into a cylindrical sock (for example—any shape may be produced) and coated with epoxy or a rubber cast molding to form the bearing. Such bearing may be used in applications in which metal bearings are insufficient. These applications include those in which dirt, water, or other contaminants that may attack metal are present, such as with anti-sway bars in automobiles and other vehicles.

The inventive fiber may also be used to produce fabric. Such fabric may be produced by weaving, braiding, knitting or needlepunching, for example. The inventive fiber may also be cut into staple and used to produce fabric such as felt. The fiber may also be towed in this application, depending on the desired properties of the fabric. Fabric formed of the inventive fiber is expected to demonstrate improved performance based on the improved fiber properties.

The fiber of the present invention also has application as an improved dental floss filament ranging in weight per length of 450 denier to 2900 denier, and preferably, 700 to 2200 denier. These filaments possess toughness greater than about 0.36 grams/denier, have widths of about 0.5 mm to about 5.0 mm, and thicknesses of about 30 μm to about 300 μm. Filaments can be optionally twisted together using two or more monofilaments. Also, a filament can be folded onto itself, or preferably, be substantially flat and unfolded.

The fiber of the present invention in all applications may optionally include one or more additives that vary depending on the application in which the fiber is used and the intended effect to be produced by the additive. Such additives include active ingredients such as stannous fluoride, medicaments, vitamins, anti-inflammatory agents, analgesics, anti-coagulents, and anti-bacterials, as well as other organic materials and inorganic material, (such as titanium dioxide to improve "grippability" of a dental floss filament), flavor-enhancing ingredients, wax (which may be added to the fiber in an amount up to about 10% by weight), thermal or electric conductives, pigments, metals, ceramics, and oxides. Other additives may also be included as will be understood by those skilled in the art. These additives may be incorporated by coating (lick or dip), spraying, powder coating, impregnation, coextrusion, or some combination of these methods, such as is taught in U.S. Pat. No. 5,262,234.

The improved properties of the fiber of this invention, specifically including peak engineering stress, break strain, and toughness, are reflected in stress-strain diagrams of the inventive fiber. To generate stress-strain diagrams, the following test was used:

High Speed Tensile Test

Testing was conducted at ambient temperature (20° C.) on a tensile test machine (Interlaken Series 3310 test system, Interlaken Technology Corp., Eden Prairie, Minn.) equipped with pneumatic fiber grips (Instron Corp., Canton, Mass.) set to a gauge length of 270 mm. For each fiber tested, denier was determined by weighing a single, one meter sample of the fiber on a Denver Instruments, Inc. Model AA160 analytical balance, and multiplying the weight, which was expressed in grams, by 9000. Five, one meter samples were randomly chosen throughout the length of a fiber to be tested. Each of the five samples was tested separately. The sample was loaded into the grips and clamped. The fiber was then slackened by moving the grips 50 mm closer together. Care was taken to make sure that the fiber did not get tangled. The test began as the grips moved apart at a cross head speed of 2000 mm/sec (±1.0%). Care was taken to ensure that constant velocity was reached at the point where the grips were 270 mm apart. A high speed data acquisition system recorded load and displacement at a rate of 2000 points/sec. The test ended when the sample broke. Each of the five randomly chosen test samples were tested.

The load data (in units of grams) for each test and displacement data (in units of millimeters) for each test were imported into a standard spreadsheet, Microsoft Excel, operating on a personal computer, a Dell Pentium 133Mhz. The spreadsheet was programmed, according to techniques well known by those skilled in the art, to normalize the load data by dividing it by the denier of the tested fiber, and to express the displacement data (the engineering strain) as a percent (displacement divided by the original fiber length tested, which was 270 mm.). The spreadsheet was also programmed, according to techniques well known by those skilled in the art, to plot the data in graph form up to the point after break where the engineering stress returns to zero. The data was examined in order to identify the peak engineering stress, the engineering strain at peak engineering stress and the break strain. The value of toughness for each sample was calculated from the following formula.

$$\text{Toughness} = \sum_{i=1}^{n} (\varepsilon_{(i+1)} - \varepsilon_i) \frac{(\sigma_i + \sigma_{(i+1)})}{2}$$

where $\varepsilon$ is engineering strain and $\sigma$ is engineering stress expressed in grams/denier, and i varies from 1 to n. n is the total number of data points for that data set.

This formula was programmed into the spreadsheet, again according to techniques well known by those skilled in the art, which calculated the toughness value for each sample according to the above formula.

The values of peak engineering stress, strain at peak engineering stress, break strain, and toughness are reported for each sample in the tables. In addition, the mean, standard deviation (Stdev), and coefficient of variation (CV) are calculated and reported based on the corresponding values for the five tested samples (unless otherwise indicated).

Suitable peak engineering stress for the PTFE fiber of this invention is greater than about 1.6 g/d, with a preferred range of from about 3.0 to about 5.0 g/d, and a most preferred peak engineering of about 4.4 g/d. Suitable break strain is greater than about 20 percent, preferably from about 20 to about 50 percent, and most preferably about 24 percent. Suitable toughness for the fiber is greater than about 0.36 g/d, preferably about 0.50 g/d to about 0.80 g/d, and most preferably about 0.60 g/d.

The invention will now be described in connection with the following examples, which are intended to be illustrative of the invention and not to limit it.

EXAMPLES

Comparative Example 1

Figure 2:
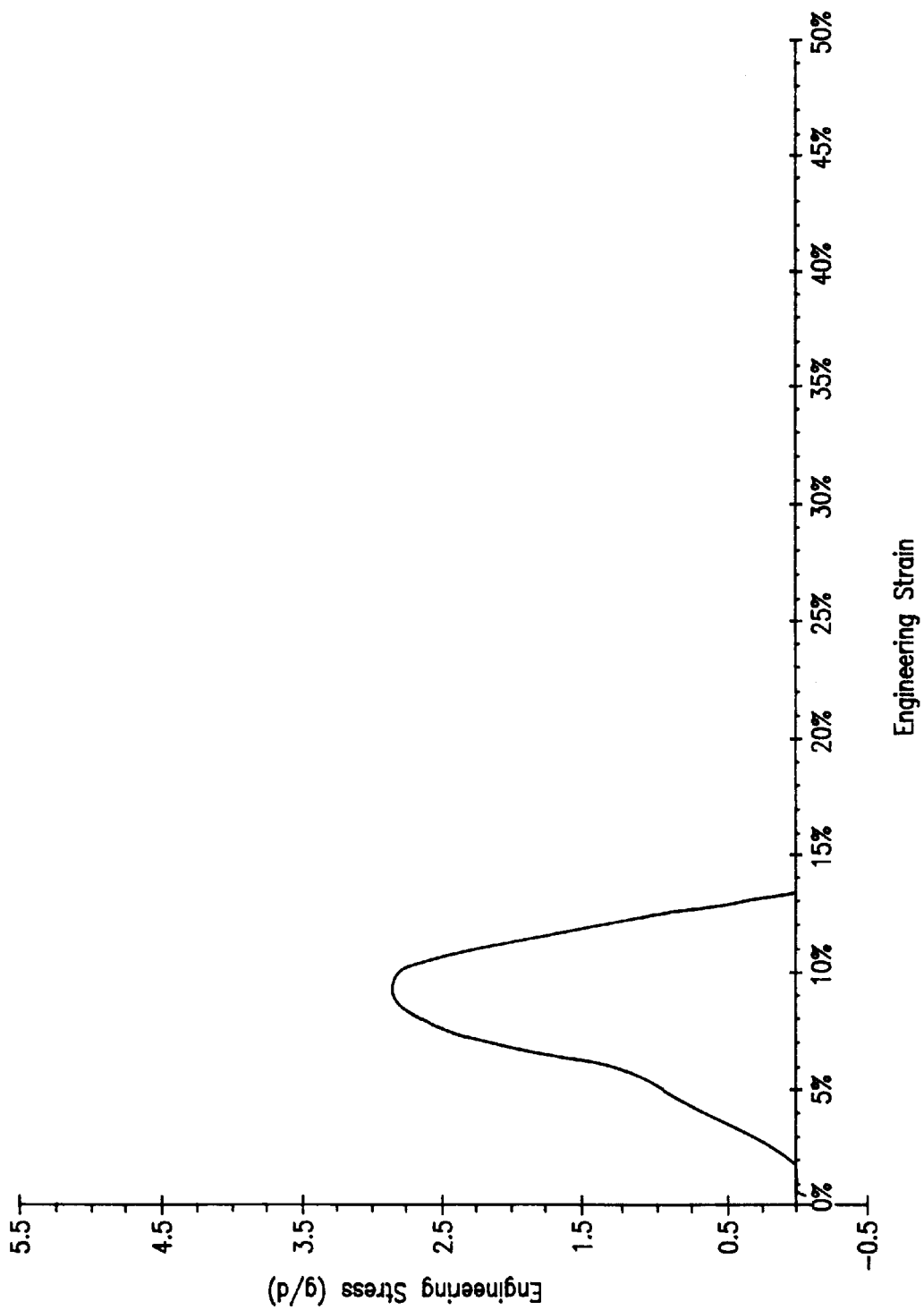
FIG. 2 is a graph illustrating the properties of a PTFE fiber before treatment according to this invention.

A sample of 1180 denier PTFE fiber sold under the trademark GORE-TEX® was obtained from W. L. Gore & Associates, Inc., Newark, Del. The fiber included 7 twists per inch in the z direction. Five samples from this fiber were tested according to the above high speed tensile test. The denier, peak engineering stress, strain at peak engineering stress, break strain, and toughness of each sample were then calculated as described above and averaged to get the mean for these properties. The measurements for the five samples, the mean, the standard deviation, and CV for this comparative example are shown below in Table I. Representative data of one of the samples is shown in graph form in the stress-strain curve of FIG. 2 (subsequent references to graphs also refer to representative data from one of several samples tested).

TABLE I

| Sample Number | Peak Engineering Stress (g/d) | Strain at Peak Engineering Stress (%) | Break Strain (%) | Toughness (g/d) |
| --- | --- | --- | --- | --- |
| 1 | 2.30 | 9.20% | 13.8% | 0.169 |
| 2 | 2.67 | 8.86% | 13.1% | 0.179 |
| 3 | 3.45 | 8.65% | 13.3% | 0.213 |
| 4 | 2.73 | 8.71% | 13.0% | 0.175 |
| 5 | 2.83 | 9.00% | 13.1% | 0.178 |
| Mean | 2.80 | 8.88% | 13.2% | 0.183 |
| Stdev | 0.42 | 0.22% | 0.30% | 0.017 |
| CV | 14.9 | 2.50 | 2.30 | 9.41 |

Comparative Example 2

Figure 2A:
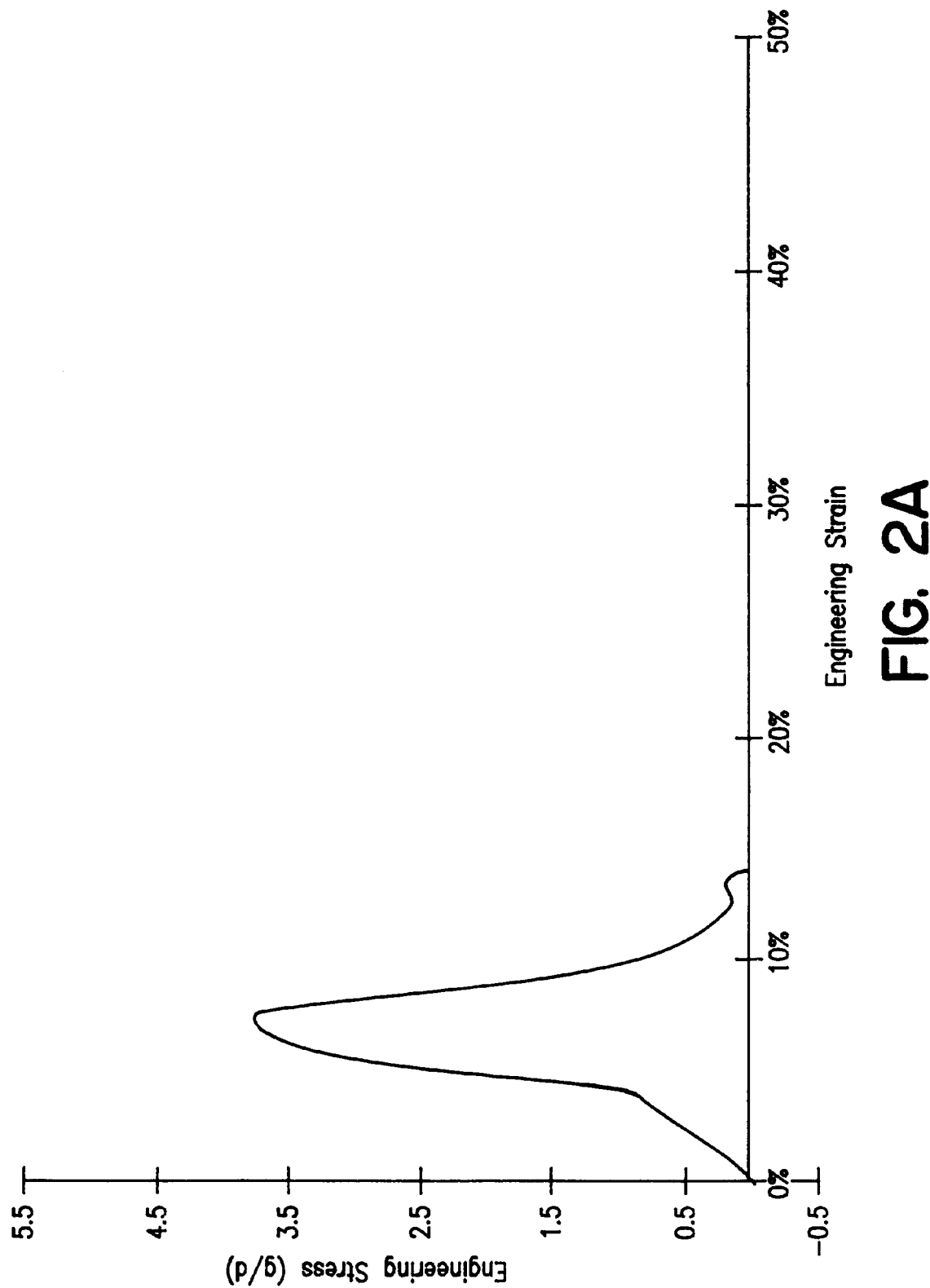
FIG. 2A is a graph illustrating the properties of another PTFE fiber before treatment according to this invention.

A sample of 1180 denier PTFE sewing thread sold under the trademark TENARA® was obtained from W. L. Gore & Associates. Five samples of this fiber were tested in the same manner and for the same properties as in Comparative Example 1. The results are presented below in Table IA. These results are shown in graph form in FIG. 2A.

TABLE IA

| Sample Number | Peak Engineering Stress (g/d) | Strain at Peak Engineering Stress (%) | Break Strain (%) | Toughness (g/d) |
| --- | --- | --- | --- | --- |
| 1 | 2.76 | 7.20% | 10.5% | 0.132 |
| 2 | 3.50 | 7.13% | 10.9% | 0.155 |
| 3 | 4.18 | 6.85% | 14.8% | 0.194 |
| 4 | 3.73 | 6.86% | 13.3% | 0.172 |
| 5 | 4.27 | 6.86% | 15.1% | 0.191 |
| Mean | 3.69 | 6.98% | 12.9% | 0.169 |
| Stdev | 0.61 | 0.17% | 2.14% | 0.026 |
| CV | 16.5 | 2.47 | 16.5 | 15.3 |

The thread of this example was tested on two needles and two bobbins of a Pfaff Model 1420 lockstitch sewing machine using an acrylic fabric. The machine could not run the fiber of this example at speeds greater than 1800 stitches per minute. At speeds above 1800 stitches per minute, the fiber broke.

Comparative Example 3

A sample of 754 denier polyester sewing thread sold under the trademark Saba 35 was obtained from Amann & Sohne GmbH & Co., Germany. Five samples of this fiber were tested in the same manner and for the same properties as in Comparative Example 1. The results are present ed below in Table IB. These results are shown in graph form in FIG. 2B.

TABLE IB

| Sample Number | Peak Engineering Stress (g/d) | Strain at Peak Engineering Stress (%) | Break Strain % | Toughness (g/d) |
| --- | --- | --- | --- | --- |
| 1 | 4.65 | 22.2% | 27.5% | 0.586 |
| 2 | 4.71 | 21.5% | 26.4% | 0.574 |
| 3 | 4.88 | 21.8% | 27.0% | 0.597 |
| 4 | 4.82 | 22.2% | 27.7% | 0.602 |
| 5 | 4.67 | 21.8% | 27.0% | 0.569 |
| Mean | 4.75 | 21.9% | 27.1% | 0.586 |
| Std Dev | 0.10 | 0.28% | 0.52% | 0.014 |
| CV | 2.13 | 1.29 | 1.92 | 2.43 |

The polyester fiber of Comparative Example 3 is typically run on the same sewing machine used in Comparative Example 2 at 2400 stitches per minute.

Example 1

The PTFE fiber of Comparative Example 1 was subjected to the process of this invention. Using nip rolls, the fiber was fed at an overfeed rate of about 13 percent over a plate heated to 400° C. The residence time of the fiber on the heated plate was 5.5 seconds. The fiber was subsequently wound onto a core. After treatment, the denier of this fiber was measured to be 1360.

Table II below shows the measurement, mean, standard deviation, and CV for five samples of this treated fiber for the same properties that were measured in Comparative Example 1. Also shown is the percent change in the treated fiber of this Example in comparison with the untreated fiber in Comparative Example 1.

TABLE II

| Sample Number | Peak Engineering Stress (g/d) | Strain at Peak Engineering Stress (%) | Break Strain (%) | Toughness (g/d) |
| --- | --- | --- | --- | --- |
| 1 | 4.35 | 18.3% | 28.0% | 0.691 |
| 2 | 4.48 | 15.6% | 24.2% | 0.614 |
| 3 | 4.47 | 16.4% | 24.4% | 0.606 |
| 4 | 4.55 | 16.2% | 24.9% | 0.655 |
| 5 | 4.09 | 14.0% | 19.0% | 0.404 |
| Mean | 4.39 | 16.1% | 24.1% | 0.594 |
| Stdev | 0.18 | 1.55% | 3.25% | 0.112 |
| CV | 4.04 | 9.60 | 13.5 | 18.8 |
| % Change | 57% | 81% | 82% | 225% |

Figure 3:
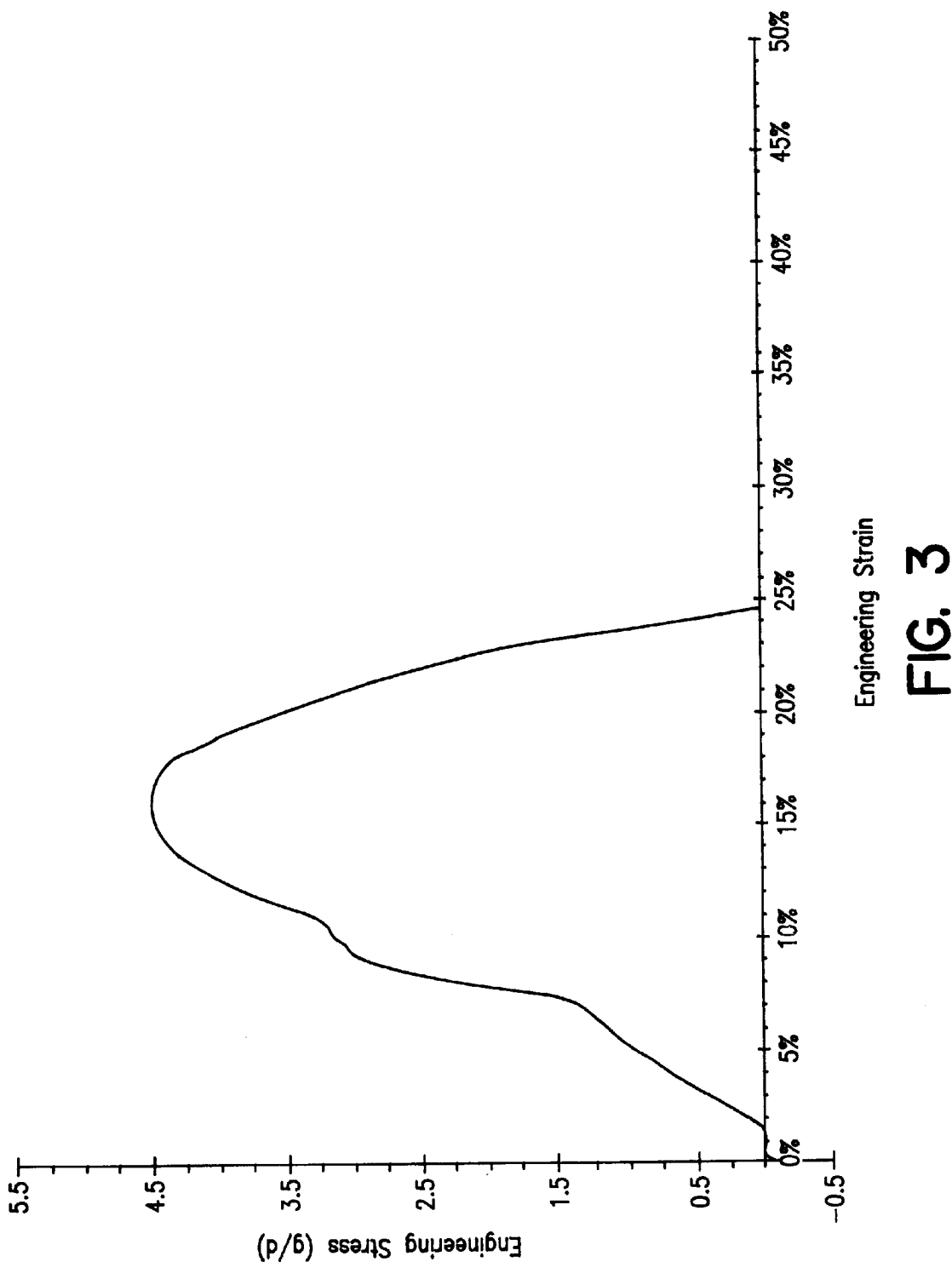
FIG. 3 is a graph illustrating the properties of a fiber after treatment with the process of this invention.

As can be seen from the data the strain at peak engineering stress, the break strain, and the toughness increased 81 percent, 82 percent and 225 percent, respectively, for the treated fiber of Example 1 over the untreated fiber of Comparative Example 1. The data for Example 1 also shows dramatic improvement in these properties when compared to those in Comparative Example 2. The data for the properties in Example 1 can be seen to compare favorably to those in Comparative Example 3 (polyester). The data for Example 1 is shown in graph form in the stress-strain curve shown in FIG. 3.

Example 1A

A sample of PTFE fiber sold under the trademark GORE-TEX® with 7 twists per inch in the Z direction was obtained from W. L. Gore & Associates, Inc. This fiber was subject to treatment according to the present invention with an overfeed of 15% and 2.5 seconds residence time on the 400° C. plate. In addition, this sample was also subject to a subsequent heat treatment step at zero percent overfeed and 2.5 seconds residence time on a 400° C. plate.

Figure 3A:
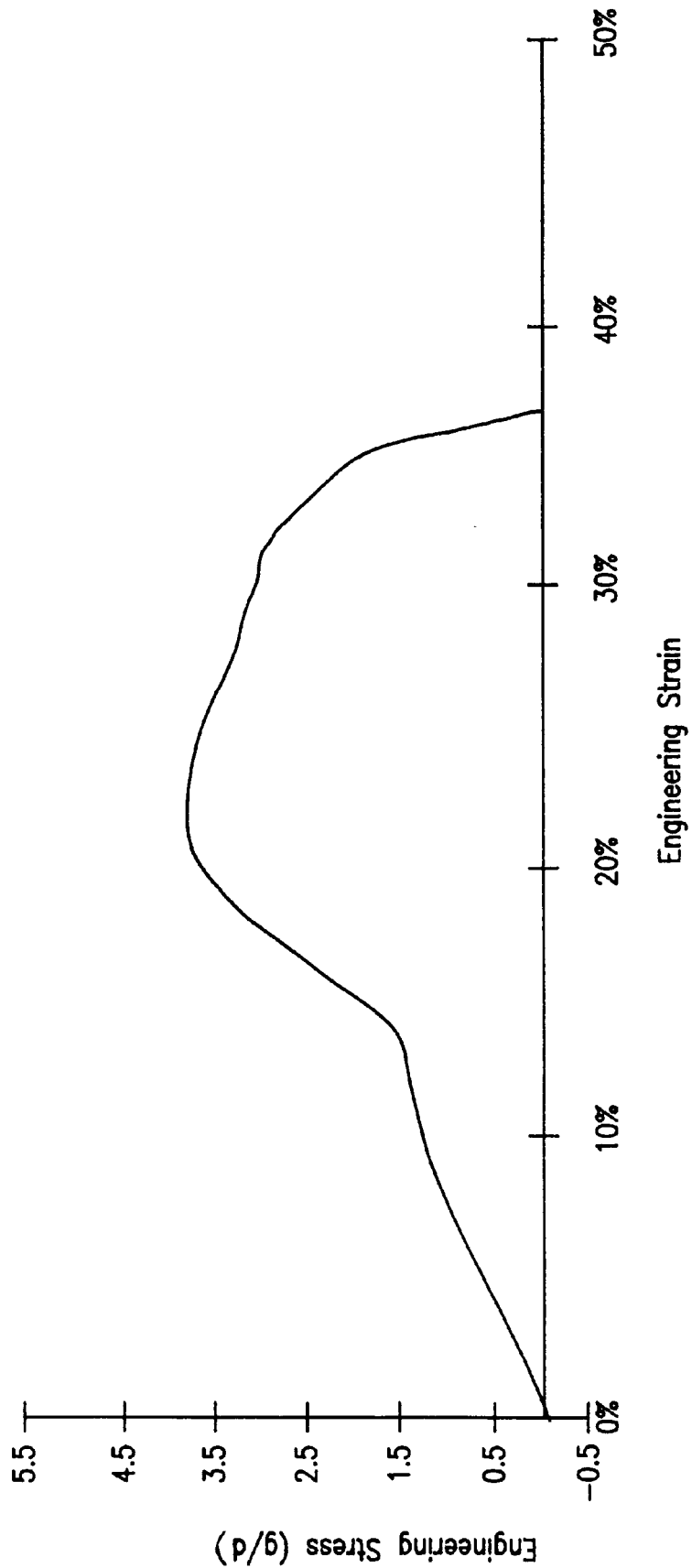
FIG. 3A is a graph illustrating the properties of a fiber after treatment with the process of this invention.

Table IIA below shows the measurement, mean, standard deviation, and CV for five samples of this treated fiber for the same properties that were measured in Comparative Example 1. The data for Example 1A can be seen to compare favorably to those in Comparative Example 3 (polyester). The data for Example 1A is shown in graph form in the stress-strain curve shown in FIG. 3A.

TABLE IIA

| Sample Number | Peak Engineering Stress (g/d) | Strain at Peak Engineering Stress (%) | Break Strain (%) | Toughness (g/d) |
| --- | --- | --- | --- | --- |
| 1 | 3.74 | 21.5% | 28.2% | 0.538 |
| 2 | 3.73 | 24.4% | 37.3% | 0.855 |
| 3 | 3.64 | 21.8% | 32.9% | 0.678 |
| 4 | 3.82 | 21.5% | 37.0% | 0.802 |
| 5 | 3.68 | 21.8% | 39.8% | 0.897 |
| Mean | 3.72 | 22.2% | 35.0% | 0.754 |
| Stdev | 0.07 | 1.24% | 4.56% | 0.146 |
| CV | 1.84 | 5.60 | 13.0 | 19.4 |

The treated fiber of Example 1A was tested on the same sewing machine used in Comparative Example 2. Using the treated fiber of this invention, the machine was able to operate at 2600 stitches per minute for 43 consecutive runs of 2.5 meters with no thread breaks. This is a dramatic improvement in sewing speed over the PTFE fiber of Comparative Example 2. The sewability performance of the treated fiber of Example 1A compares favorably to that of the polyester fiber of Comparative Example 3. The PTFE fiber of this invention can be much more easily and quickly sewn in comparison to conventional PTFE fiber because of its enhanced properties and sewability, producing many advantages and efficiencies in use.

Comparative Example 4

Figure 4:
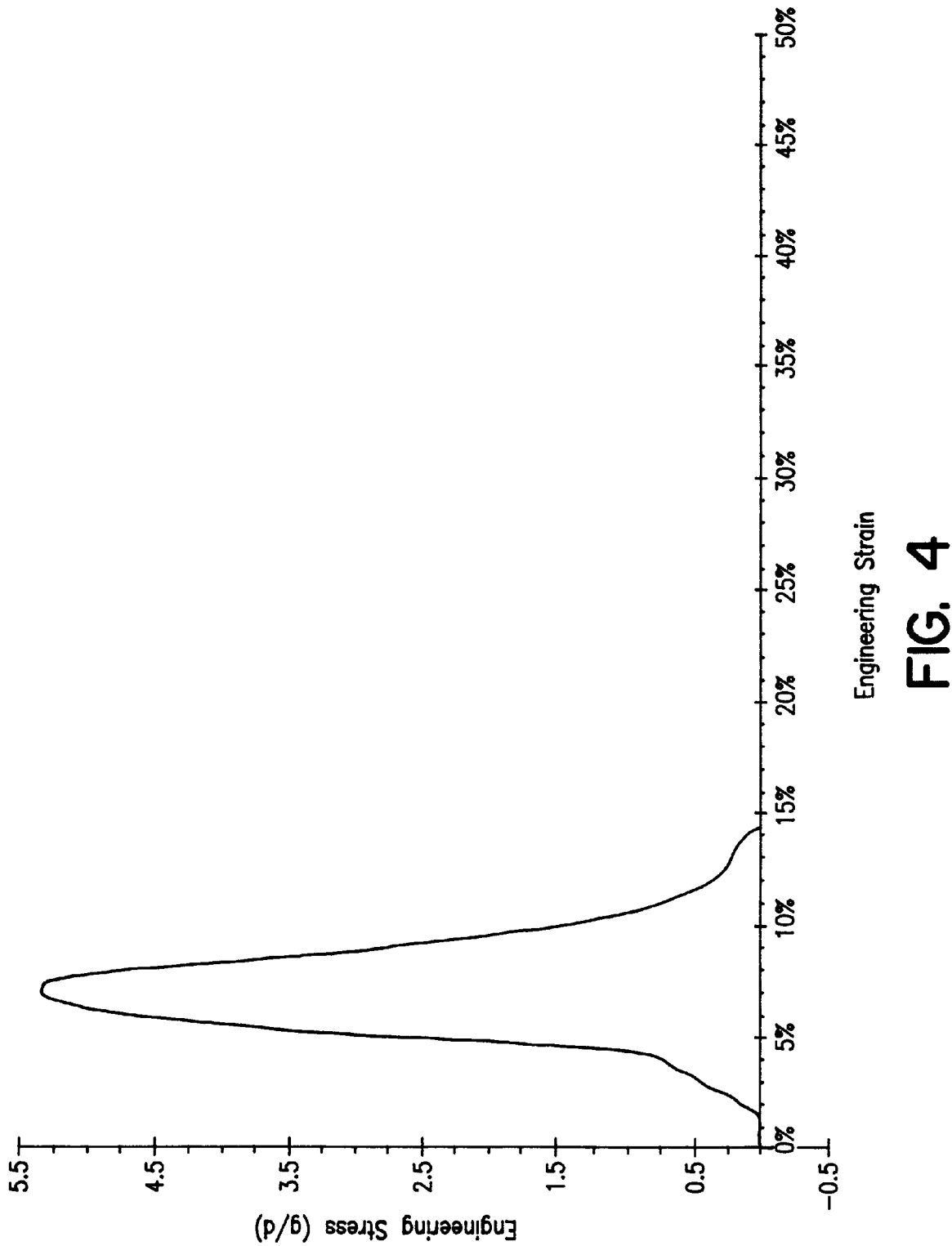
FIG. 4 is a graph illustrating the properties of a fiber before treatment with the process of this invention.

A sample of flat, white, 1320 denier PTFE fiber sold under the trademark GORE-TEX® was obtained from W. L. Gore & Associates, Inc. Five samples of this fiber were tested in the same manner and for the same properties as in Comparative Example 1. The results are presented in Table III below. The data for this comparative example are represented in graph form in FIG. 4.

TABLE III

| Sample Number | Peak Engineering Stress (g/d) | Strain at Peak Engineering Stress (%) | Break Strain (%) | Toughness (g/d) |
| --- | --- | --- | --- | --- |
| 1 | 3.43 | 7.34% | 11.6% | 0.185 |
| 2 | 1.49 | 7.96% | 11.5% | 0.097 |
| 3 | 5.54 | 7.47% | 13.3% | 0.281 |
| 4 | 5.31 | 7.47% | 13.2% | 0.263 |
| 5 | 5.31 | 7.11% | 14.4% | 0.250 |
| Mean | 4.22 | 7.47% | 12.8% | 0.215 |
| Stdev | 1.75 | 0.31% | 1.3% | 0.075 |
| CV | 41.4 | 4.14 | 9.83 | 35.0 |

Example 2

Figure 5:
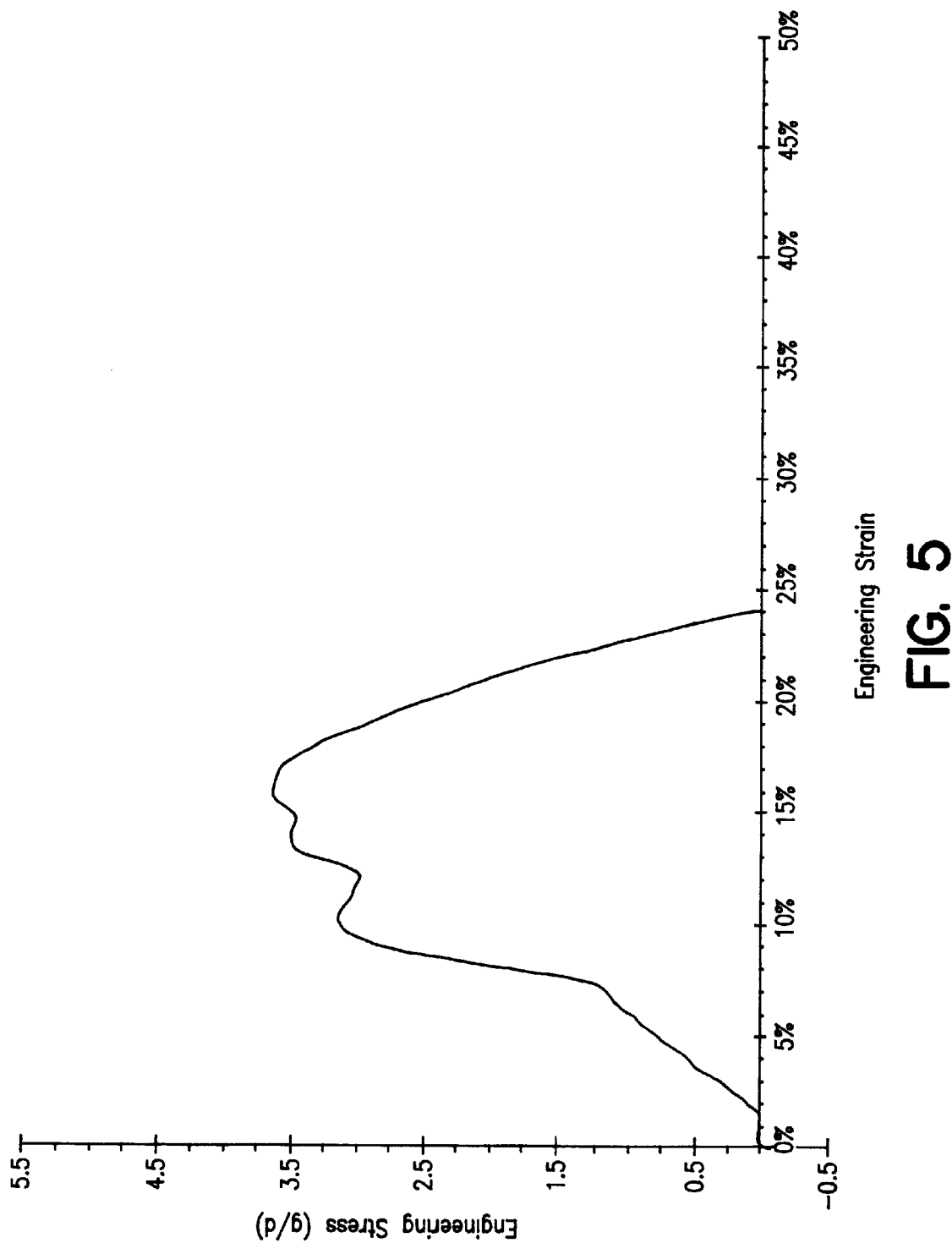
FIG. 5 is a graph illustrating the properties of a fiber after treatment with the process of this invention.

The flat, white, PTFE fiber of Comparative Example 4 was treated by the process of this invention using the same conditions as defined in Example 1. After treatment, the denier of this fiber was measured to be 1560. The same tests were also performed and the results are presented below in Table IV and in graph form in FIG. 5. This data indicates dramatic improvements over the fiber of Comparative Example 4 in the strain at peak engineering stress, the break strain, and the toughness of the fiber after treatment according to the inventive process. Because the values of the measured properties are similar to those in Example 1A, the fiber of this Example 2 will perform well in applications that require improved toughness. The fiber of this Example 2 will perform better in such applications than the fiber of Comparative Example 4 because of the enhanced properties of the fiber of Example 2.

TABLE IV

| Sample Number | Peak Engineering Stress (g/d) | Strain at Peak Engineering Stress (%) | Break Strain (%) | Toughness (g/d) |
| --- | --- | --- | --- | --- |
| 1 | 3.56 | 19.3% | 36.8% | 0.883 |
| 2 | 3.75 | 15.5% | 21.6% | 0.446 |
| 3 | 3.63 | 16.7% | 23.9% | 0.494 |
| 4 | 3.87 | 16.6% | 25.6% | 0.580 |
| 5 | 3.22 | 10.4% | 19.0% | 0.326 |
| Mean | 3.60 | 15.7% | 25.4% | 0.546 |
| Stdev | 0.25 | 3.25% | 6.84% | 0.210 |
| CV | 6.80 | 20.7 | 26.9 | 38.4 |

Comparative Example 5

Figure 6:
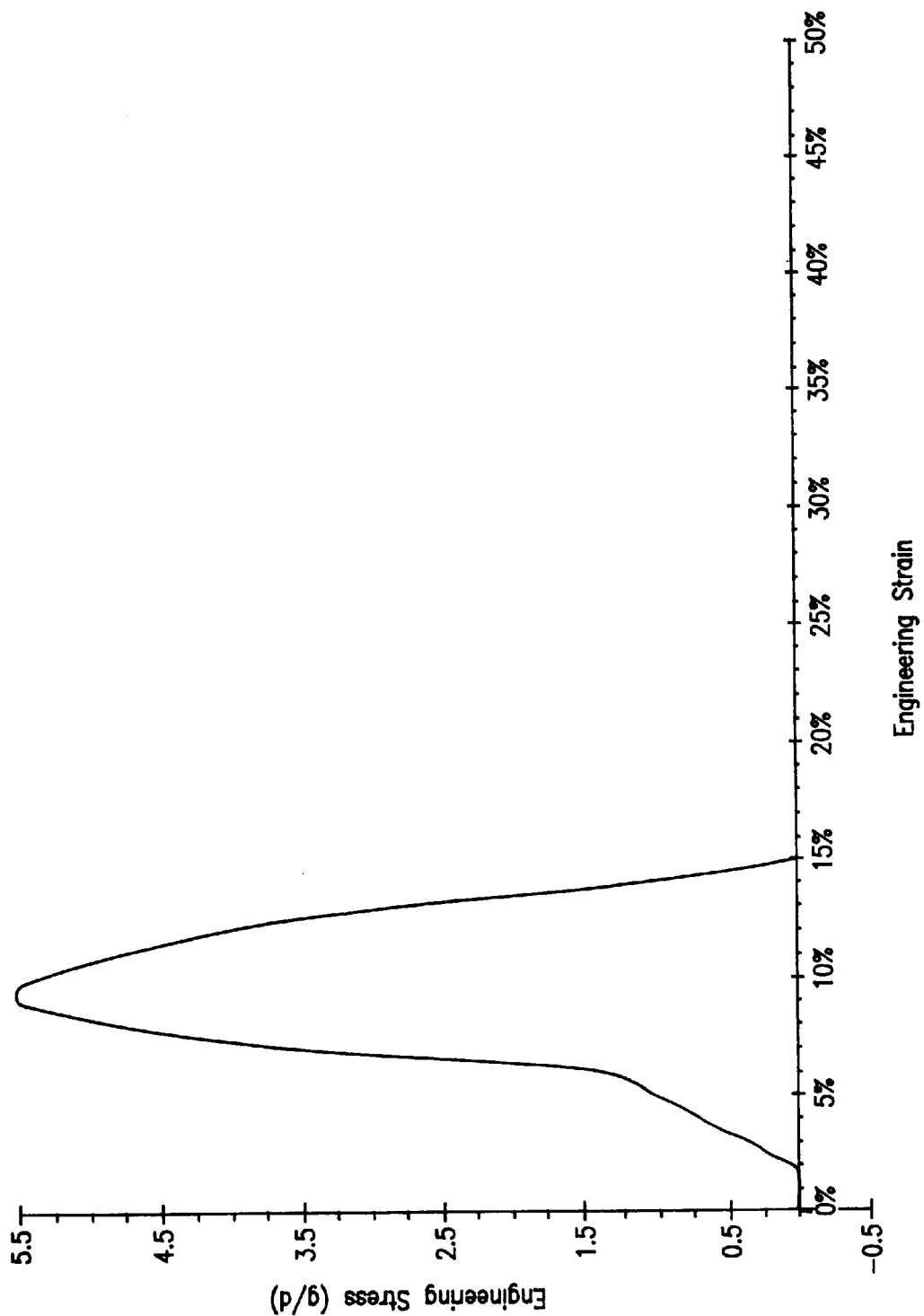
FIG. 6 is a graph illustrating the properties of a fiber before treatment with the process of this invention.

A sample of flat, black, 1250 denier PTFE fiber sold under the trademark GORE-TEX® was obtained from W. L. Gore & Associates, Inc. Five samples of this fiber were tested in the same manner and for the same properties as in Comparative Example 1. The results are presented in Table V below. The data for this comparative example are represented in graph form in FIG. 6.

TABLE V

| Sample Number | Peak Engineering Stress (g/d) | Strain at Peak Engineering Stress (%) | Break Strain (%) | Toughness (g/d) |
| --- | --- | --- | --- | --- |
| 1 | 4.84 | 9.62% | 14.92% | 0.287 |
| 2 | 4.99 | 9.53% | 15.60% | 0.353 |
| 3 | 5.28 | 9.75% | 14.85% | 0.331 |
| 4 | 5.44 | 9.39% | 15.04% | 0.356 |
| 5 | 6.56 | 10.9% | 16.22% | 0.464 |
| Mean | 5.42 | 9.84% | 15.33% | 0.358 |
| Stdev | 0.68 | 0.61% | 0.58% | 0.065 |
| CV | 12.5 | 6.23 | 3.78 | 18.2 |

Example 3

Figure 7:
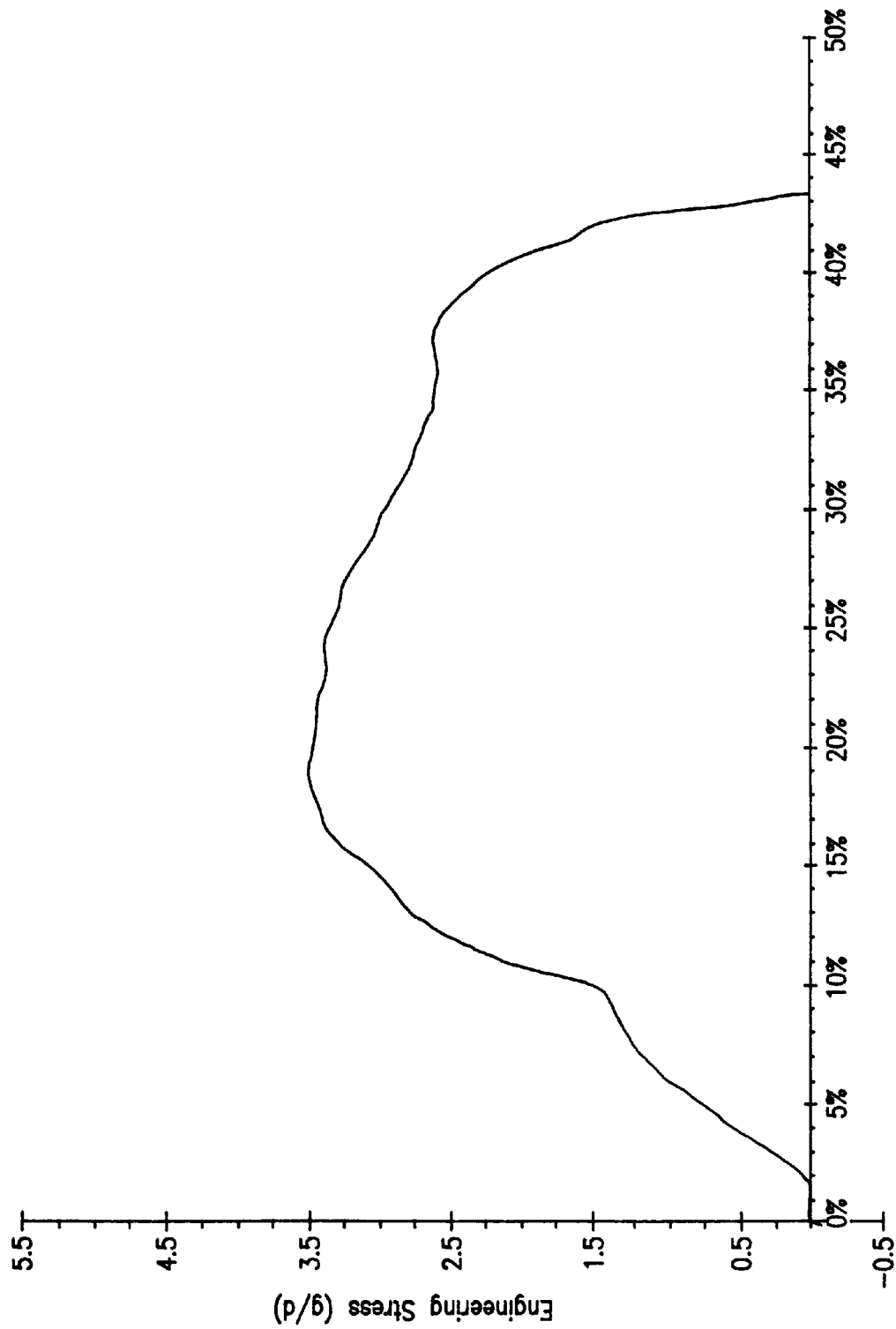
FIG. 7 is a graph illustrating the properties of a fiber after treatment with the process of this invention.

The flat, black, PTFE fiber of Comparative Example 5 was treated by the process of this invention using the same conditions as defined in Example 1. After treatment, the denier of this fiber was measured to be 1450. The same tests were also performed and the results are presented below in Table VI and in graph form in FIG. 7. This data indicates dramatic improvements over the fiber of Comparative Example 5 in the strain at peak engineering stress, the break strain, and the toughness of the fiber after treatment according to the inventive process. Because the values of the measured properties are similar to those in Example 1A, the fiber of this Example 3 will perform well in applications that require improved toughness. The fiber of this Example 3 will likely perform better in such applications than the fiber of Comparative Example 5 because of the enhanced properties of the fiber of Example 3.

TABLE VI

| Sample Number | Peak Engineering Stress (g/d) | Strain at Peak Engineering Stress (%) | Break Strain (%) | Toughness (g/d) |
| --- | --- | --- | --- | --- |
| 1 | 3.49 | 18.6% | 50.5% | 1.15 |
| 2 | 3.40 | 19.3% | 43.9% | 0.991 |
| 3 | 3.40 | 19.0% | 43.3% | 0.979 |
| 4 | 3.44 | 17.9% | 40.4% | 0.918 |
| 5 | 3.34 | 17.1% | 46.6% | 1.03 |
| Mean | 3.41 | 18.3% | 45.0% | 1.01 |
| Stdev | 0.06 | 0.89% | 3.83% | 0.086 |
| CV | 1.62 | 4.84 | 8.51 | 8.50 |

Comparative Example 6

Figure 8:
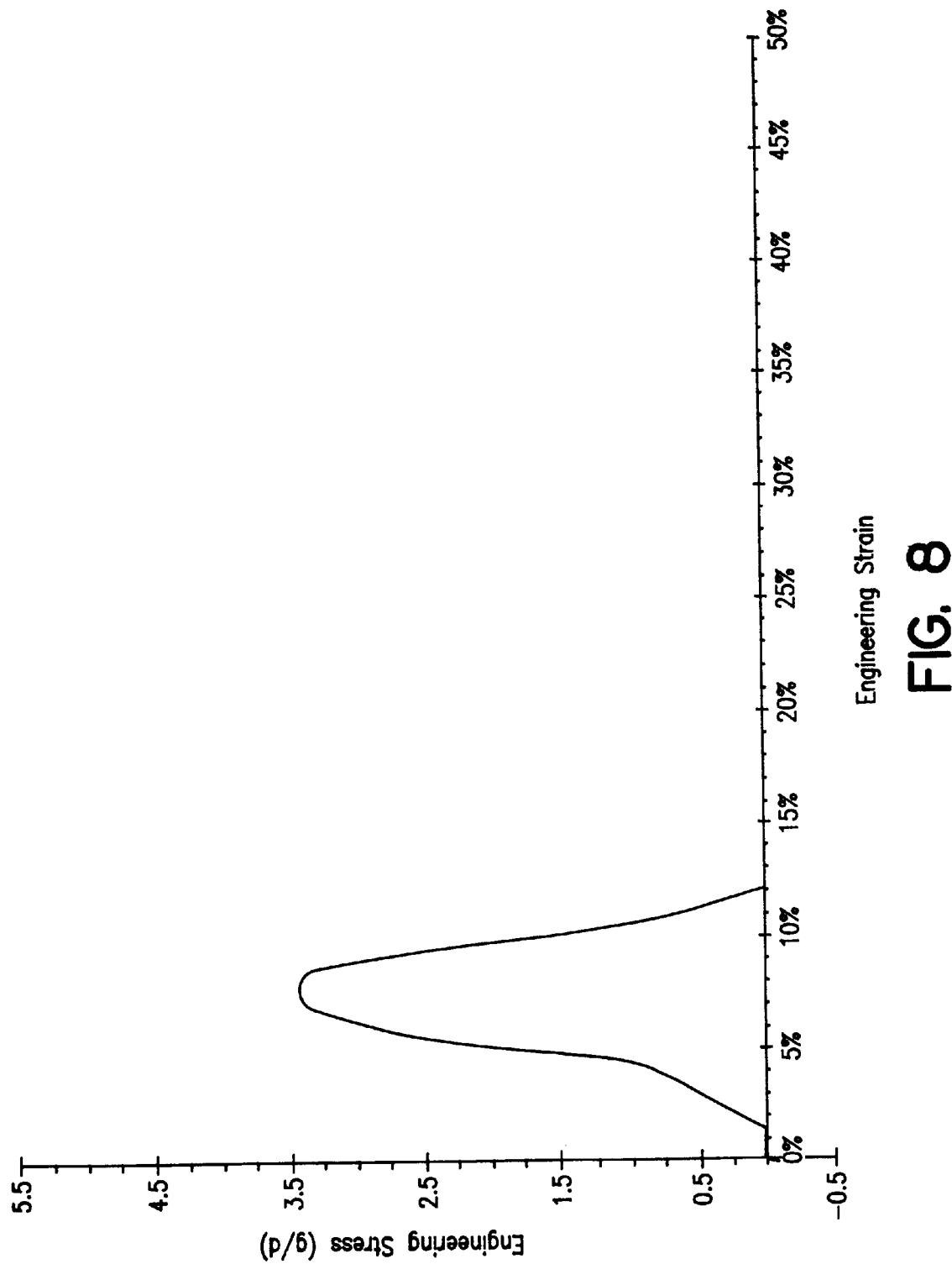
FIG. 8 is a graph illustrating the properties of a fiber before treatment with the process of this invention.

A flat, red, 1250 denier PTFE fiber sold under the trademark GORE-TEX® was obtained from W. L. Gore & Associates, Inc. Five samples of this fiber were tested in the same manner and for the same properties as in Comparative Example 1. The results are presented in Table VII below. The data for this comparative example are represented in graph form in FIG. 8.

TABLE VII

| Sample Number | Peak Engineering Stress (g/d) | Strain at Peak Engineering Stress (%) | Break Strain (%) | Toughness (g/d) |
| --- | --- | --- | --- | --- |
| 1 | 4.04 | 7.13% | 12.2% | 0.215 |
| 2 | 3.58 | 7.20% | 11.8% | 0.198 |
| 3 | 3.79 | 7.48% | 12.1% | 0.194 |
| 4 | 3.32 | 7.55% | 11.8% | 0.175 |
| 5 | 2.18 | 9.07% | 12.9% | 0.143 |
| Mean | 3.38 | 7.69% | 12.1% | 0.185 |
| Stdev | 0.72 | 0.79% | 0.44% | 0.027 |
| CV | 21.4 | 10.30 | 3.60 | 14.7 |

Example 4

Figure 9:
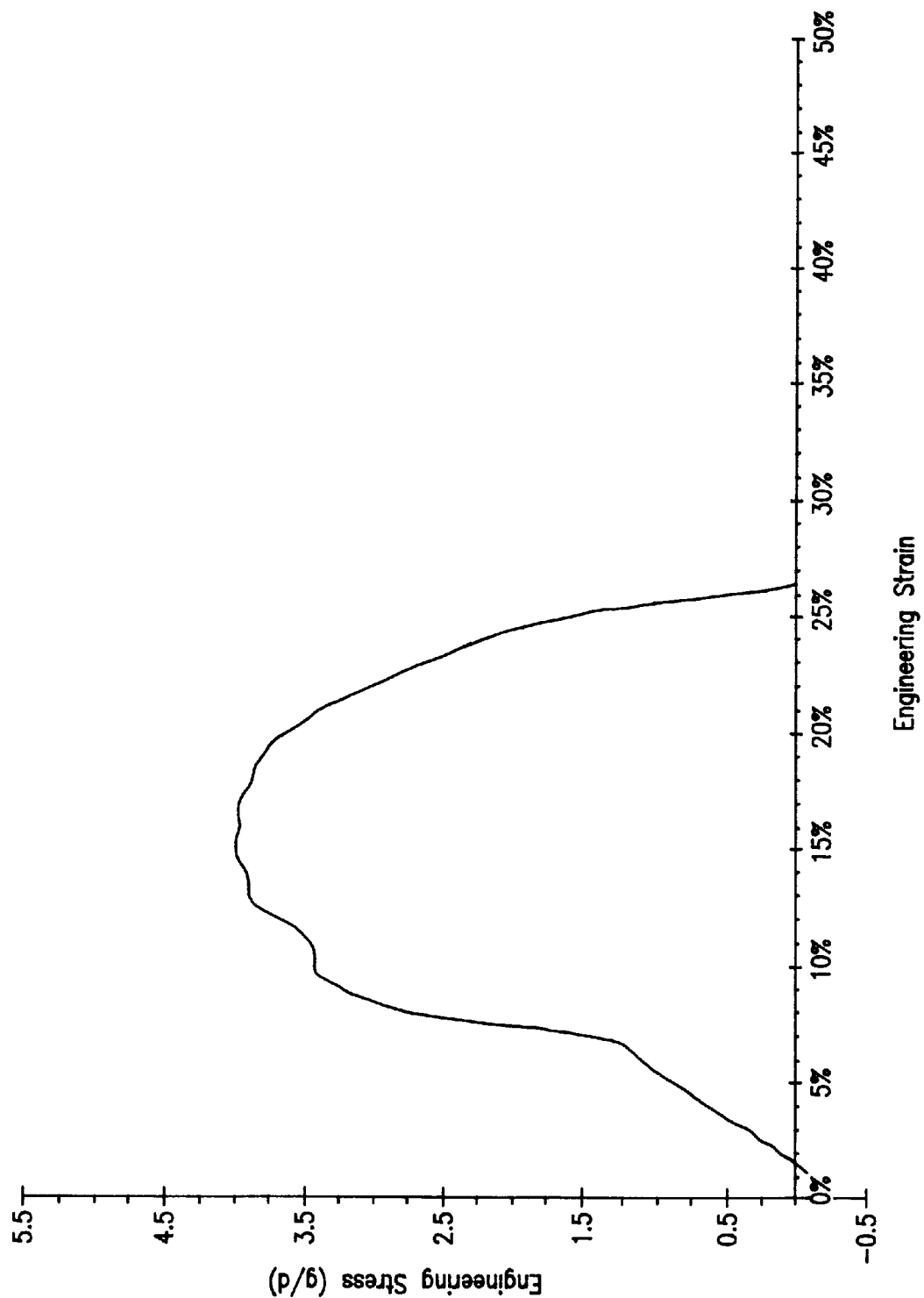
FIG. 9 is a graph illustrating the properties of a fiber after treatment with the process of this invention.

The flat, red, PTFE fiber of Comparative Example 6 was treated by the process of this invention using the same conditions as defined in Example 1. After treatment, the denier of this fiber was measured to be 1450. The same tests were also performed and the results are presented below in Table VIII and in graph form in FIG. 9. This data indicates dramatic improvements over the fiber of Comparative Example 6 in the strain at peak engineering stress, the break strain, and the toughness of the fiber after treatment according to the inventive process. Because the values of the measured properties are similar to those in Example 1A, the fiber of this Example 4 will perform well in applications that require improved toughness. The fiber of the Example 4 will likely perform better in such applications than the fiber of Comparitive Example 6 because of the enhanced properties of the fiber of Example 4.

TABLE VIII

| Sample Number | Peak Engineering Stress (g/d) | Strain at Peak Engineering Stress (%) | Break Strain (%) | Toughness (g/d) |
| --- | --- | --- | --- | --- |
| 1 | 3.50 | 14.5% | 21.3% | 0.378 |
| 2 | 4.04 | 16.2% | 22.3% | 0.483 |
| 3 | 3.94 | 15.0% | 26.3% | 0.640 |
| 4 | 3.56 | 14.6% | 19.3% | 0.372 |
| 5 | 3.62 | 18.5% | 31.5% | 0.737 |
| Mean | 03.73 | 15.8% | 24.1% | 0.522 |
| Stdev | 0.24 | 1.67% | 4.85% | 0.162 |
| CV | 6.52 | 10.6 | 20.1 | 31.0 |

Comparative Example 7

Figure 10:
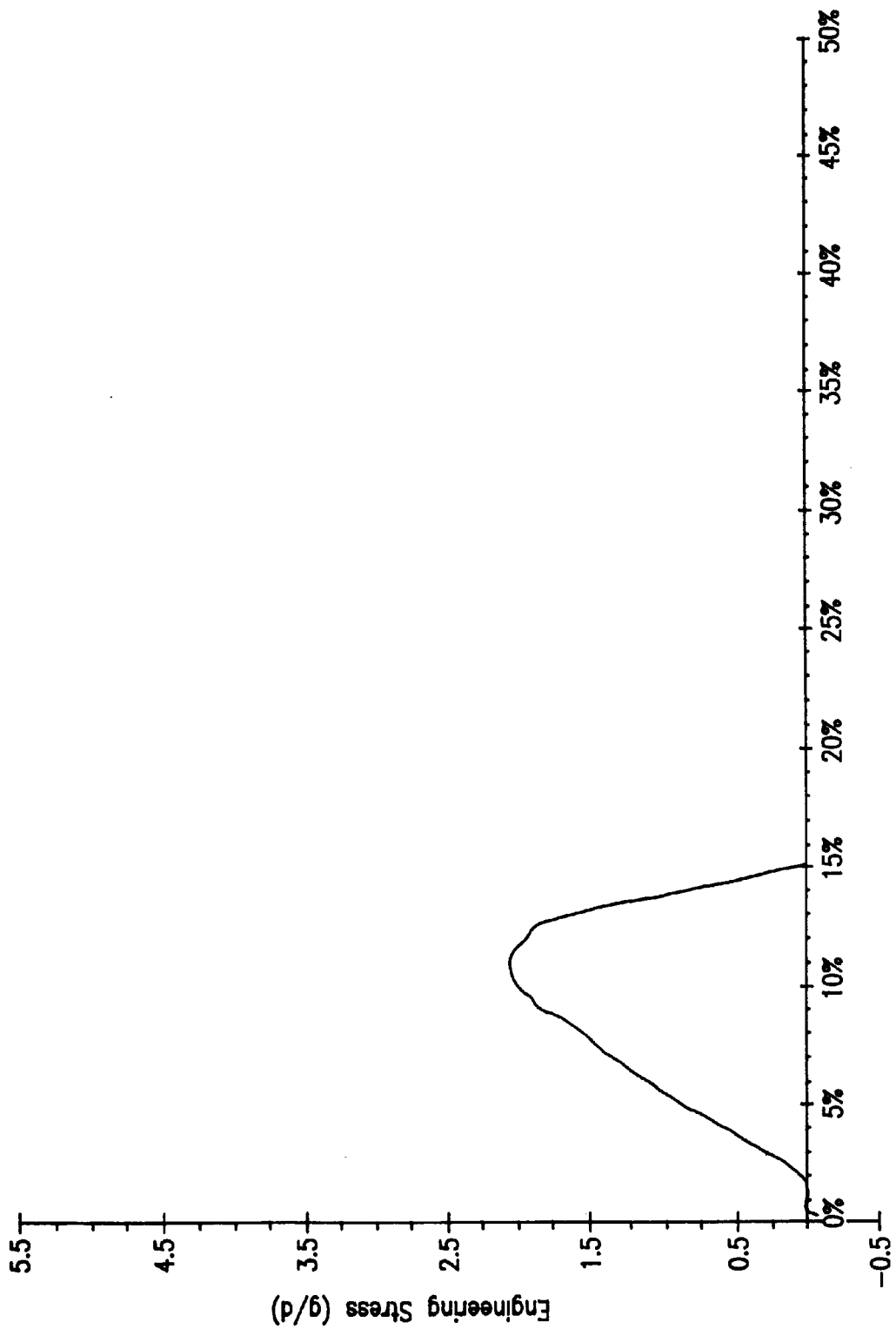
FIG. 10 is a graph illustrating the properties of a fiber before treatment with the process of this invention.

A sample of 1200 denier PROFILEN® sewing thread was obtained from Lenzing Aktiengesellschaft, Lenzing, Austria. Five samples of this fiber were tested in the same manner and for the same properties as in Comparative Example 1. The results are presented in Table IX below. The data for this example are represented in graph form in FIG. 10.

TABLE IX

| Sample Number | Peak Engineering Stress (g/d) | Strain at Peak Engineering Stress (%) | Break Strain (%) | Toughness (g/d) |
| --- | --- | --- | --- | --- |
| 1 | 1.96 | 10.8% | 15.7% | 0.171 |
| 2 | 1.92 | 11.0% | 15.2% | 0.165 |
| 3 | 1.74 | 10.2% | 13.7% | 0.143 |
| 4 | 2.50 | 10.2% | 14.9% | 0.189 |
| 5 | 2.05 | 10.5% | 15.1% | 0.164 |
| Mean | 2.03 | 10.5% | 14.9% | 0.166 |
| Stdev | 0.29 | 0.34% | 0.72% | 0.016 |
| CV | 14.08 | 3.23 | 4.84 | 9.76 |

Example 5

Figure 11:
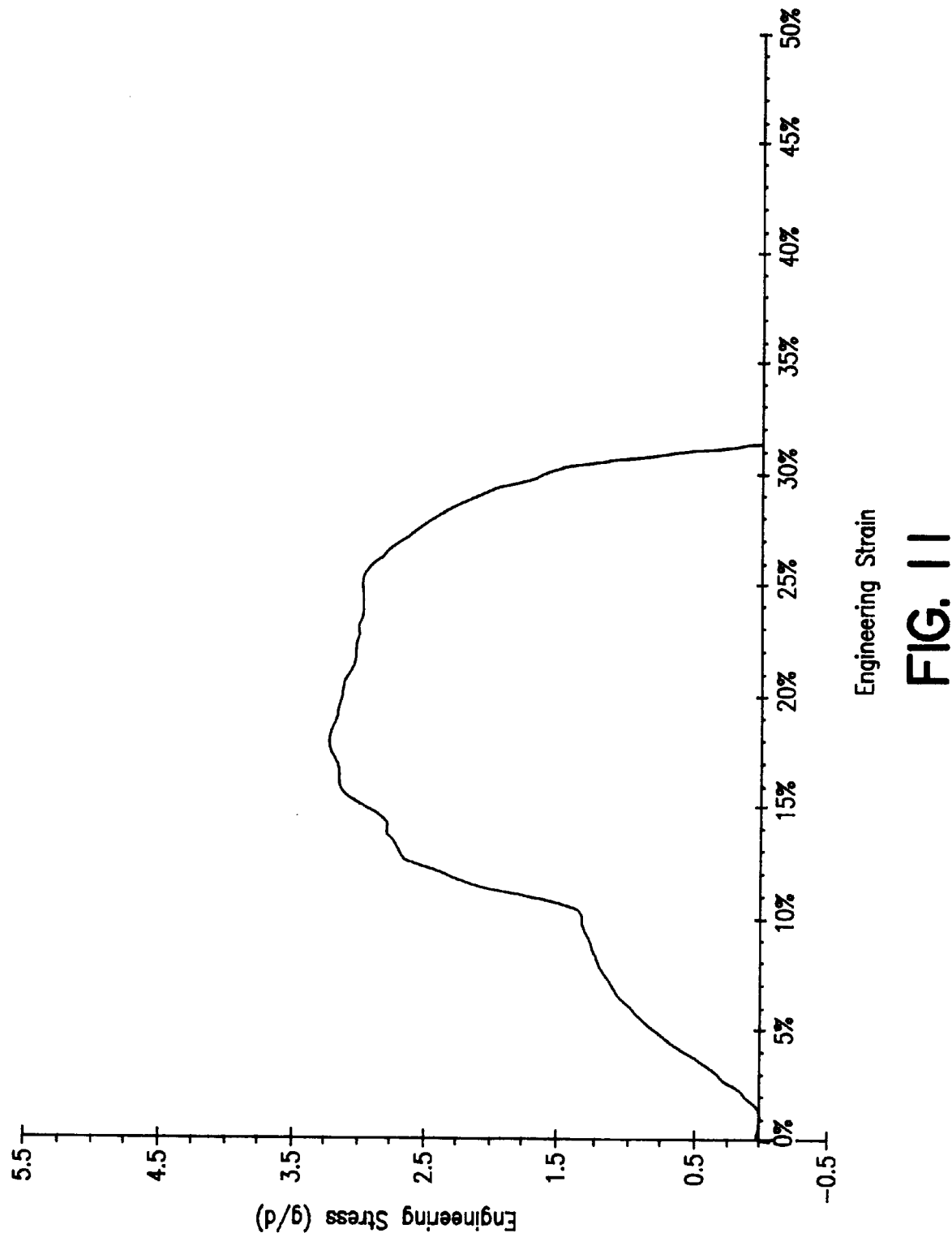
FIG. 11 is a graph illustrating the properties of a fiber after treatment with the process of this invention.

The PROFILEN® sewing thread of Comparative Example 7 was treated by the process of this invention using the same conditions as defined in Example 1. After treatment, the denier of this fiber was measured to be 1410. The same tests were also performed and the results are presented below in Table X and in graph form in FIG. 11 This data indicates dramatic improvements over the fiber of Comparative Example 7 in the strain at peak engineering stress, the break strain, and the toughness of the fiber after treatment according to the inventive process. Because the values of the measured properties are similar to those in Example 1A, the fiber of this Example 5 will perform well in applications that require improved toughness. The fiber of this Example 5 will likely perform better in such applications than the fiber of Comparative Example 7 because of the enhanced properties of the fiber of Example 5.

TABLE X

| Sample Number | Peak Engineering Stress (g/d) | Strain at Peak Engineering Stress (%) | Break Strain (%) | Toughness (g/d) |
| --- | --- | --- | --- | --- |
| 1 | 3.35 | 18.8% | 34.3% | 0.707 |
| 2 | 3.22 | 18.3% | 31.6% | 0.616 |
| 3 | 3.20 | 19.0% | 33.5% | 0.690 |
| 4 | 3.22 | 17.5% | 31.0% | 0.630 |
| 5 | 3.22 | 13.6% | 32.1% | 0.643 |
| Mean | 3.24 | 17.4% | 32.5% | 0.657 |
| Stdev | 0.06 | 2.21% | 1.36% | 0.039 |
| CV | 1.92 | 12.7 | 4.19 | 5.99 |

Comparative Example 8

Figure 12:
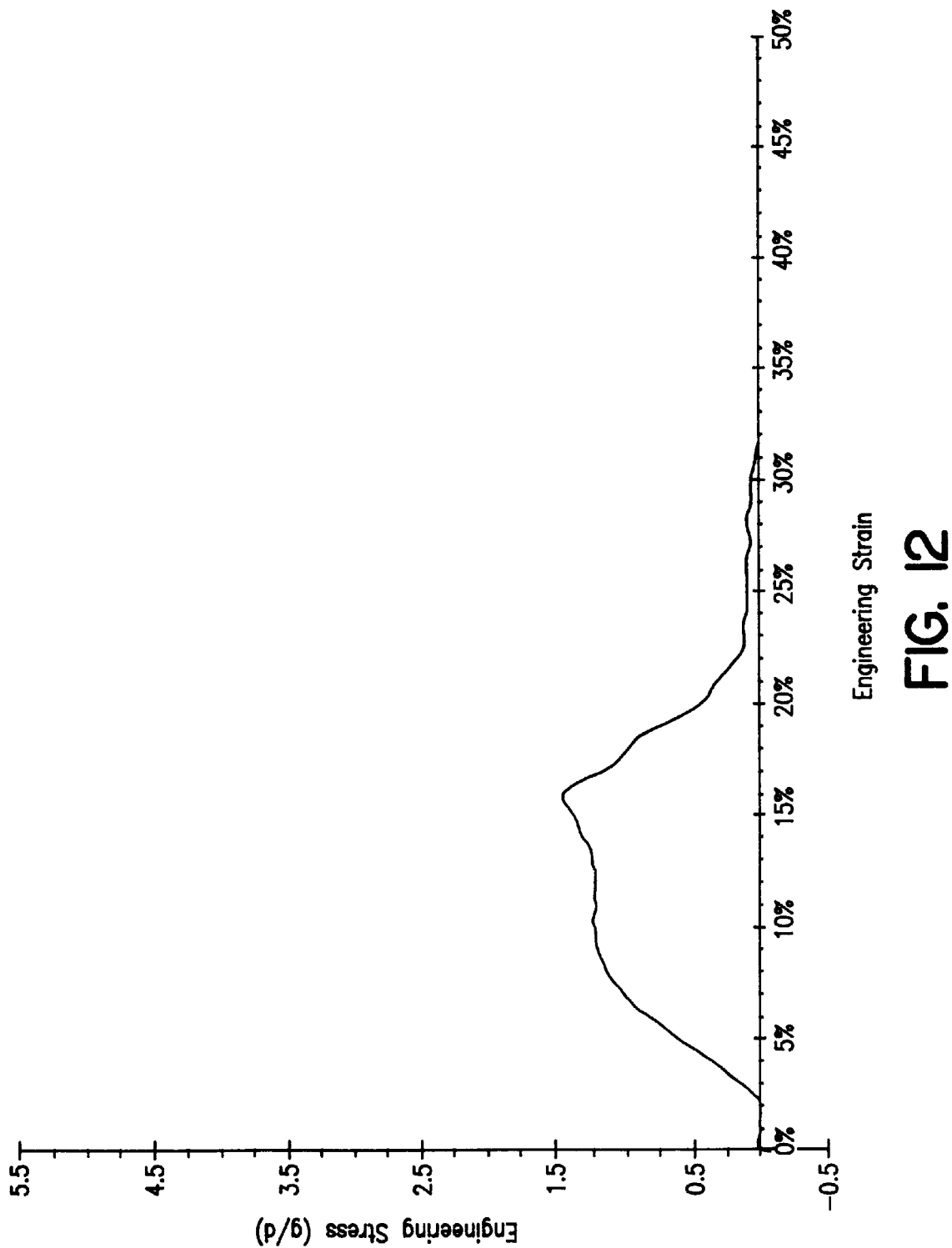
FIG. 12 is a graph illustrating the properties of a fiber before treatment with the process of this invention.

A sample of emulsion-spun brown 881 denier TEFLON® sewing thread was obtained from Synthetic Thread, Inc. of Bethlehem, Pa (TEFLON is a trademark of E.I. duPont de Nemours & Co., Inc.). Five samples of this fiber were tested in the same manner and for the same properties as in Comparative Example 1. The results are presented in Table XI below. The data for this example are represented in graph form in FIG. 12.

TABLE XI

| Sample Number | Peak Engineering Stress (g/d) | Strain at Peak Engineering Stress (%) | Break Strain (%) | Toughness (g/d) |
| --- | --- | --- | --- | --- |
| 1 | 1.57 | 91.4% | 24.6% | 0.177 |
| 2 | 1.57 | 91.4% | 25.7% | 0.186 |
| 3 | 1.59 | 91.5% | 31.0% | 0.175 |
| 4 | 1.62 | 91.6% | 32.6% | 0.176 |
| 5 | 1.60 | 91.6% | 31.7% | 0.168 |
| Mean | 1.59 | 91.5% | 29.1% | 0.176 |
| Stdev | 0.02 | 0.09% | 3.69% | 0.006 |
| CV | 1.33 | 0.10 | 12.7 | 3.62 |

Example 6

Figure 13:
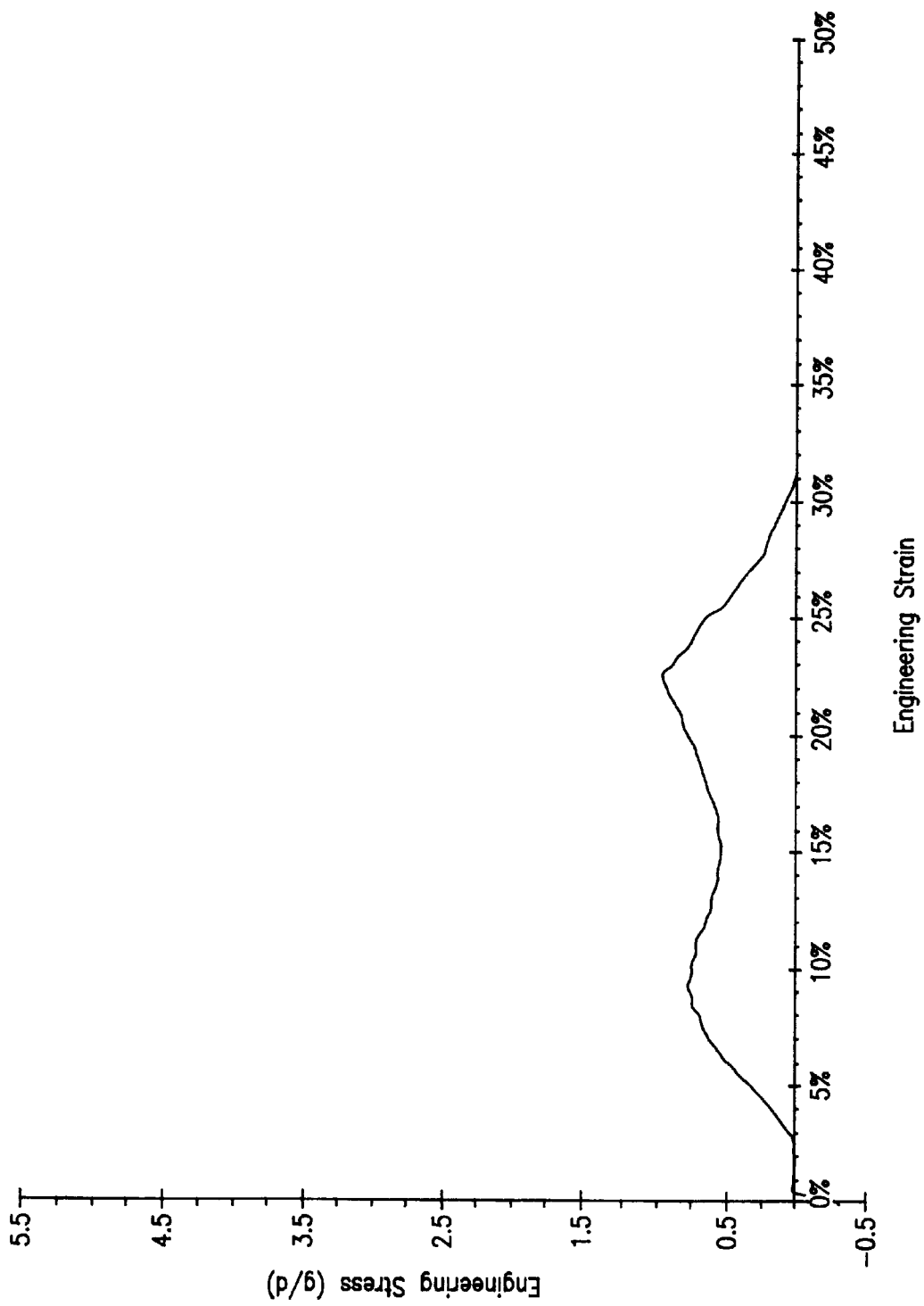
FIG. 13 is a graph illustrating the properties of a fiber after treatment with the process of this invention.

The emulsion-spun brown TEFLON sewing thread of Comparative Example 8 was treated by the process of this invention using the same conditions as defined in Example 1, except that the processing temperature was 375° C. After treatment, the denier of this fiber was measured to be 1020. The same tests were also performed and the results are presented below in The XII and in graph form in FIG. 13. This data indicates dramatic improvements over the fiber of Comparative Example 8 in the strain at peak engineering stress, the break strain, and the toughness of the fiber after treatment according to the inventive process. The fiber of this Example 6 will likely perform better than the fiber of Comparative Example 8 in applications that require increased toughness.

TABLE XII

| Sample Number | Peak Engineering Stress (g/d) | Strain at Peak Engineering Stress (%) | Break Strain (%) | Toughness (g/d) |
| --- | --- | --- | --- | --- |
| 1 | 1.56 | 91.4% | 45.2% | 0.298 |
| 2 | 1.56 | 91.4% | 44.4% | 0.294 |
| 3 | 1.39 | 91.6% | 45.9% | 0.307 |
| 4 | 1.41 | 35.7% | 42.6% | 0.287 |
| 5 | 1.39 | 34.6% | 41.1% | 0.281 |
| Mean | 1.46 | 68.9% | 43.8% | 0.293 |
| Stdev | 0.09 | 30.8% | 1.94% | 0.010 |
| CV | 6.10 | 44.7 | 4.43 | 3.53 |

Examples Demonstrating the Effect of Varying Overfeeds

Example 7

Figure 14:
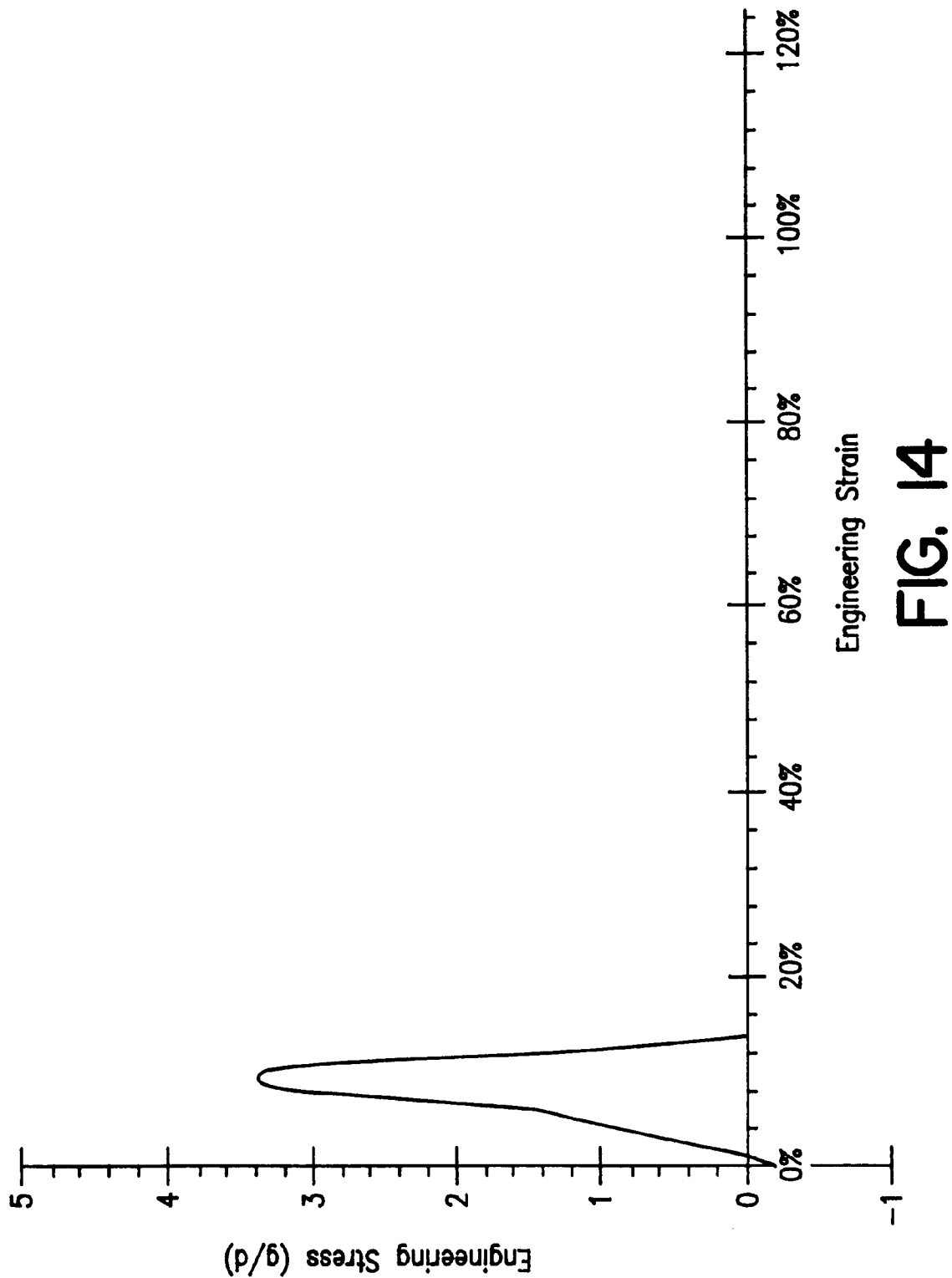
FIG. 14 is a graph illustrating the properties of a fiber using the process of the present invention with zero percent overfeed.

A sample of PTFE fiber sold under the trademark GORE-TEX® with 7 twists per inch in the z direction was obtained from W. L. Gore & Associates, Inc. This fiber was subjected to treatment according to the present invention with zero percent overfeed, with the other conditions being the same as those in Example 1. After treatment, the denier of this fiber was measured to be 1050. The data from this Example are shown below in Table XIII. The data are represented in graph form in FIG. 14.

TABLE XIII

| Sample Number | Peak Engineering Stress (g/d) | Strain at Peak Engineering Stress (%) | Break Strain (%) | Toughness (g/d) |
| --- | --- | --- | --- | --- |
| 1 | 4.30 | 8.26% | 12.8% | 0.233 |
| 2 | 5.70 | 8.73% | 16.8% | 0.298 |
| 3 | 2.11 | 9.50% | 14.8% | 0.177 |
| 4 | 2.22 | 9.12% | 14.1% | 0.176 |
| 5 | 3.33 | 9.00% | 13.6% | 0.213 |
| Mean | 3.53 | 8.92% | 14.4% | 0.219 |
| Stdev | 1.50 | 0.46% | 1.51% | 0.050 |
| CV | 42.6 | 5.20 | 10.5 | 22.8 |

Example 8

Figure 15:
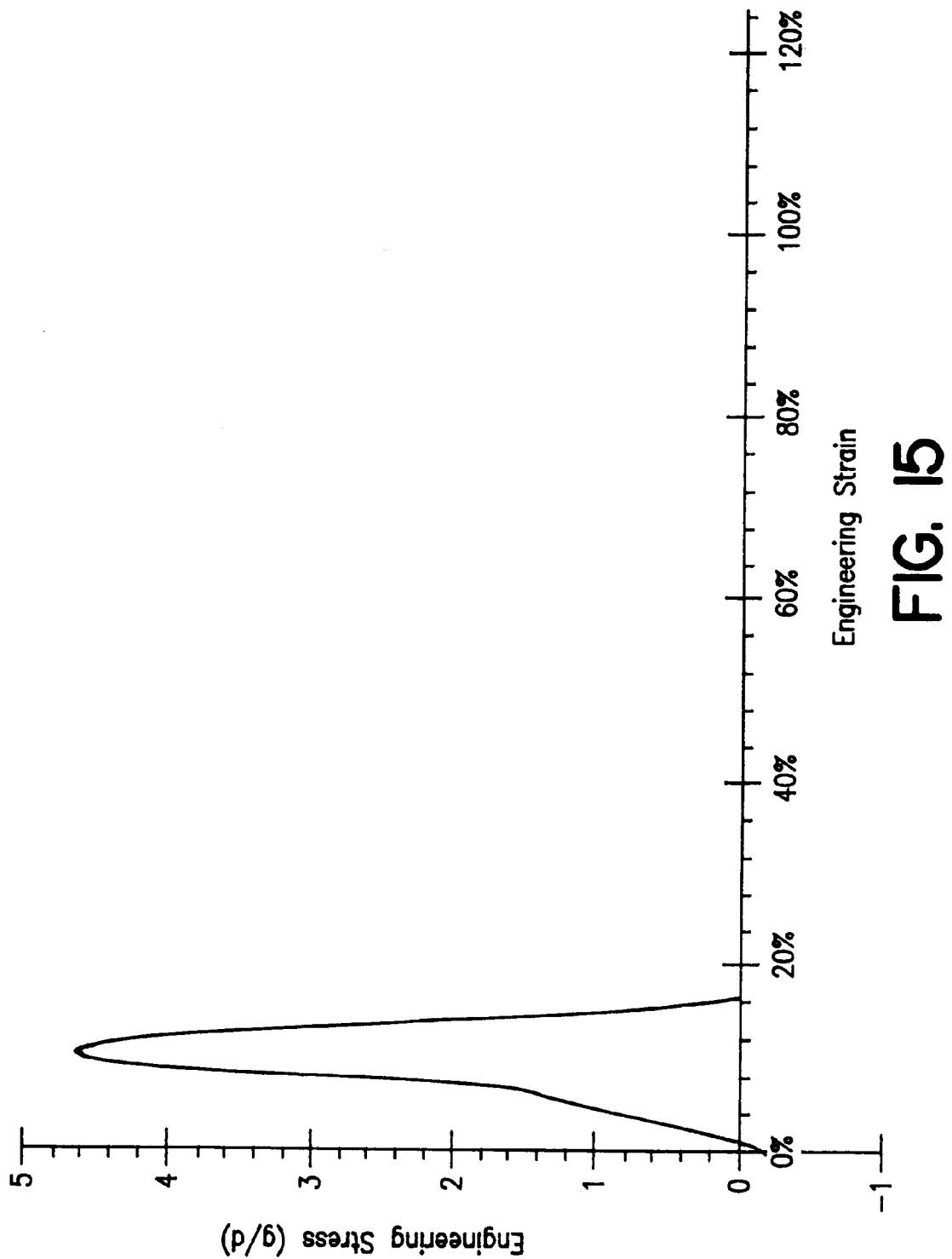
FIG. 15 is a graph illustrating the properties of a fiber using the process of the present invention with 6 percent overfeed.

A sample of PTFE fiber sold under the trademark GORE-TEX® with 7 twists per inch in the Z direction was obtained from W. L. Gore & Associates, Inc. This fiber was subjected to treatment according to the present invention with 6 percent overfeed, with the other conditions being the same as those in Example 1. After treatment, the denier of this fiber was measured to be 1120. The data from this Example are shown below in Table XIV. The data are represented in graph form in FIG. 15.

TABLE XIV

| Sample Number | Peak Engineering Stress (g/d) | Strain at Peak Engineering Stress (%) | Break Strain (%) | Toughness (g/d) |
| --- | --- | --- | --- | --- |
| 1 | 4.64 | 9.89% | 14.9% | 0.282 |
| 2 | 4.56 | 10.3% | 14.9% | 0.271 |
| 3 | 4.54 | 10.7% | 17.4% | 0.383 |
| 4 | 4.63 | 10.2% | 16.4% | 0.333 |

TABLE XIV-continued

| Sample Number | Peak Engineering Stress (g/d) | Strain at Peak Engineering Stress (%) | Break Strain (%) | Toughness (g/d) |
|---|---|---|---|---|
| 5 | 4.68 | 10.7% | 17.5% | 0.396 |
| Mean | 4.61 | 10.3% | 16.2% | 0.333 |
| Stdev | 0.06 | 0.33% | 1.32% | 0.057 |
| CV | 1.20 | 3.17 | 8.11 | 17.1 |

Example 9

Figure 16:
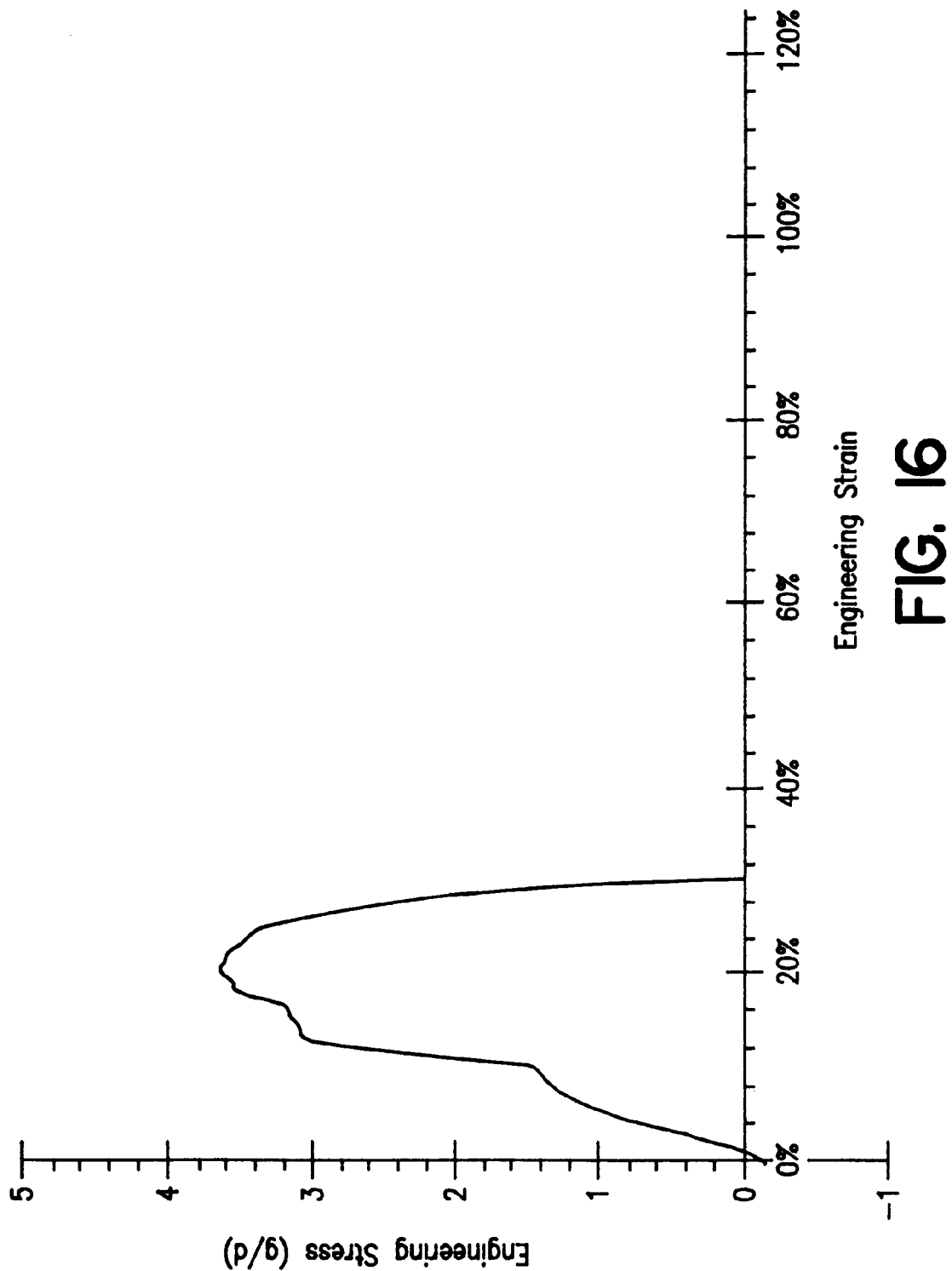
FIG. 16 is a graph illustrating the properties of a fiber using the process of the present invention with 13 percent overfeed.

A sample of PTFE fiber sold under the trademark GORE-TEX® with 7 twists per inch in the Z direction was obtained from W. L. Gore & Associates, Inc. This fiber was subjected to treatment according to the present invention with 13 percent overfeed, with the other conditions being the same as those in Example 1. After treatment, the denier of this fiber was measured to be 1270. The data from this Example are shown below in Table XV. The data are represented in graph form in FIG. 16.

TABLE XV

| Sample Number | Peak Engineering Stress (g/d) | Strain at Peak Engineering Stress (%) | Break Strain (%) | Toughness (g/d) |
|---|---|---|---|---|
| 1 | 3.56 | 19.2% | 31.5% | 0.728 |
| 2 | 3.63 | 18.90% | 32.3% | 0.725 |
| 3 | 3.59 | 17.85% | 28.2% | 0.624 |
| 4 | 3.63 | 20.0% | 30.1% | 0.690 |
| 5 | 3.66 | 19.0% | 26.1% | 0.544 |
| Mean | 3.61 | 19.0% | 29.6% | 0.662 |
| Stdev | 0.04 | 0.81% | 2.53% | 0.078 |
| CV | 1.07 | 4.28 | 8.53 | 11.8 |

Example 10

Figure 17:
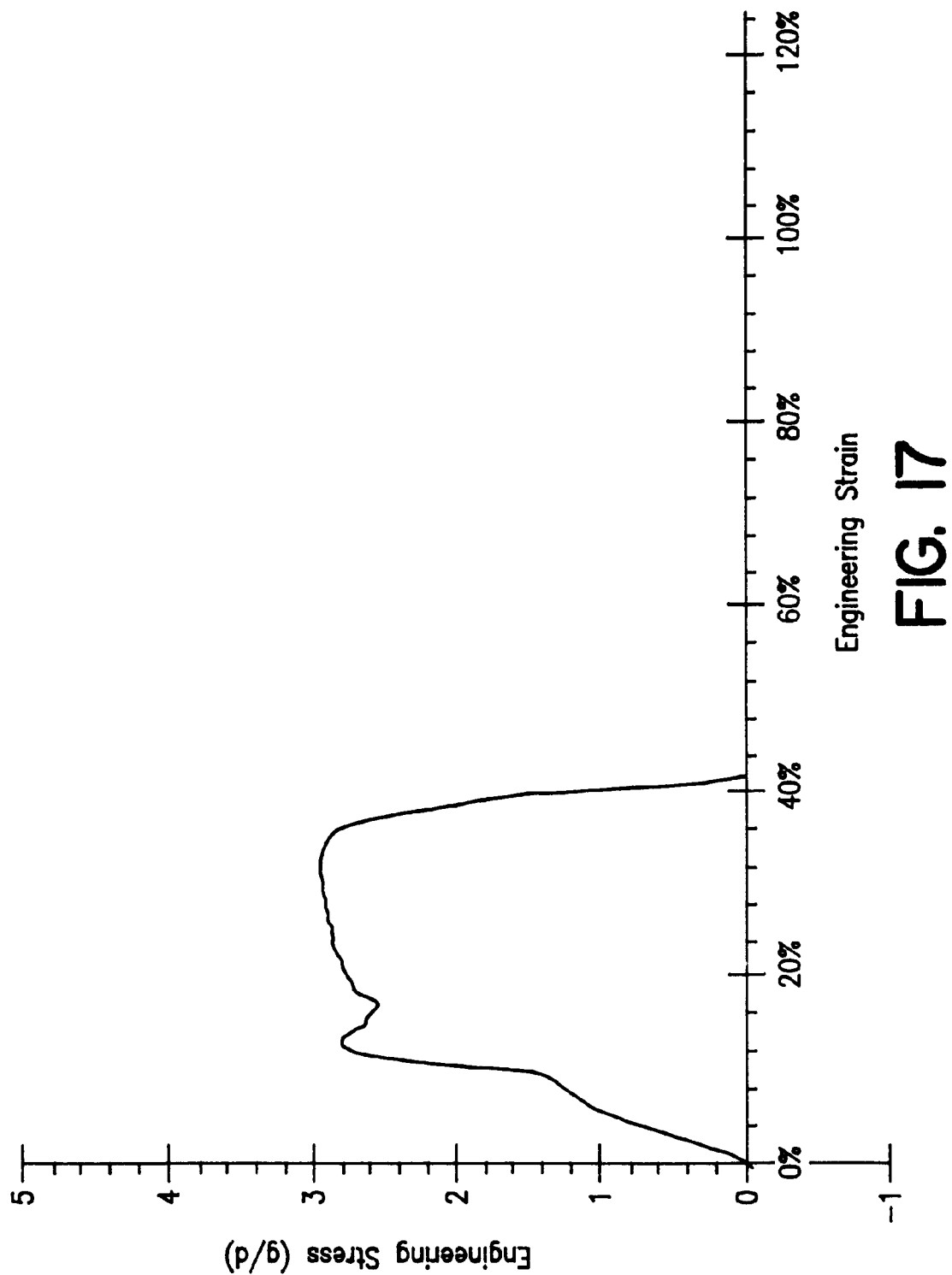
FIG. 17 is a graph illustrating the properties of a fiber using the process of the present invention with 21 percent overfeed.

A sample of PTFE fiber sold under the trademark GORE-TEX® with 7 twists per inch in the Z direction was obtained from W. L. Gore & Associates, Inc. This fiber was subjected to treatment according to the present invention with 21 percent overfeed, with the other conditions being the same as those in Example 1. After treatment, the denier of this fiber was measured to be 1330. The data from this Example are shown below in Table XVI. The data are represented in graph form in FIG. 17.

TABLE XVI

| Sample Number | Peak Engineering Stress (g/d) | Strain at Peak Engineering Stress (%) | Break Strain (%) | Toughness (g/d) |
|---|---|---|---|---|
| 1 | 2.93 | 28.0% | 41.9% | 0.923 |
| 2 | 2.94 | 30.9% | 41.8% | 0.905 |
| 3 | 2.98 | 29.7% | 45.0% | 0.990 |
| 4 | 2.82 | 28.0% | 36.4% | 0.719 |
| 5 | 2.98 | 23.0% | 36.0% | 0.749 |
| Mean | 2.93 | 27.9% | 40.2% | 0.857 |
| Stdev | 0.07 | 3.01% | 3.92% | 0.117 |
| CV | 2.30 | 10.8 | 9.75 | 13.7 |

Example 11

Figure 18:
FIG. 18 is a graph illustrating the properties of a fiber using the process of the present invention with 29 percent overfeed.

A sample of PTFE fiber sold under the trademark GORE-TEX® with 7 twists per inch in the Z direction was obtained from W. L. Gore & Associates, Inc. This fiber was subjected to treatment according to the present invention with 29 percent overfeed, with the other conditions being the same as those in Example 1. After treatment, the denier of this fiber was measured to be 1550. The data from this Example are shown below in Table XVII. The data are represented in graph form in FIG. 18.

TABLE XVII

| Sample Number | Peak Engineering Stress (g/d) | Strain at Peak Engineering Stress (%) | Break Strain (%) | Toughness (g/d) |
|---|---|---|---|---|
| 1 | 2.36 | 12.9% | 58.6% | 1.04 |
| 2 | 2.47 | 12.3% | 43.7% | 0.761 |
| 3 | 2.30 | 12.8% | 62.9% | 1.18 |
| 4 | 2.25 | 50.8% | 67.6% | 1.18 |
| 5 | 2.25 | 51.27% | 63.3% | 1.14 |
| Mean | 2.35 | 22.2% | 58.2% | 1.04 |
| Stdev | 0.10 | 19.1% | 10.4% | 0.198 |
| CV | 4.09 | 85.8 | 17.8 | 19.0 |

Example 12

Figure 19:
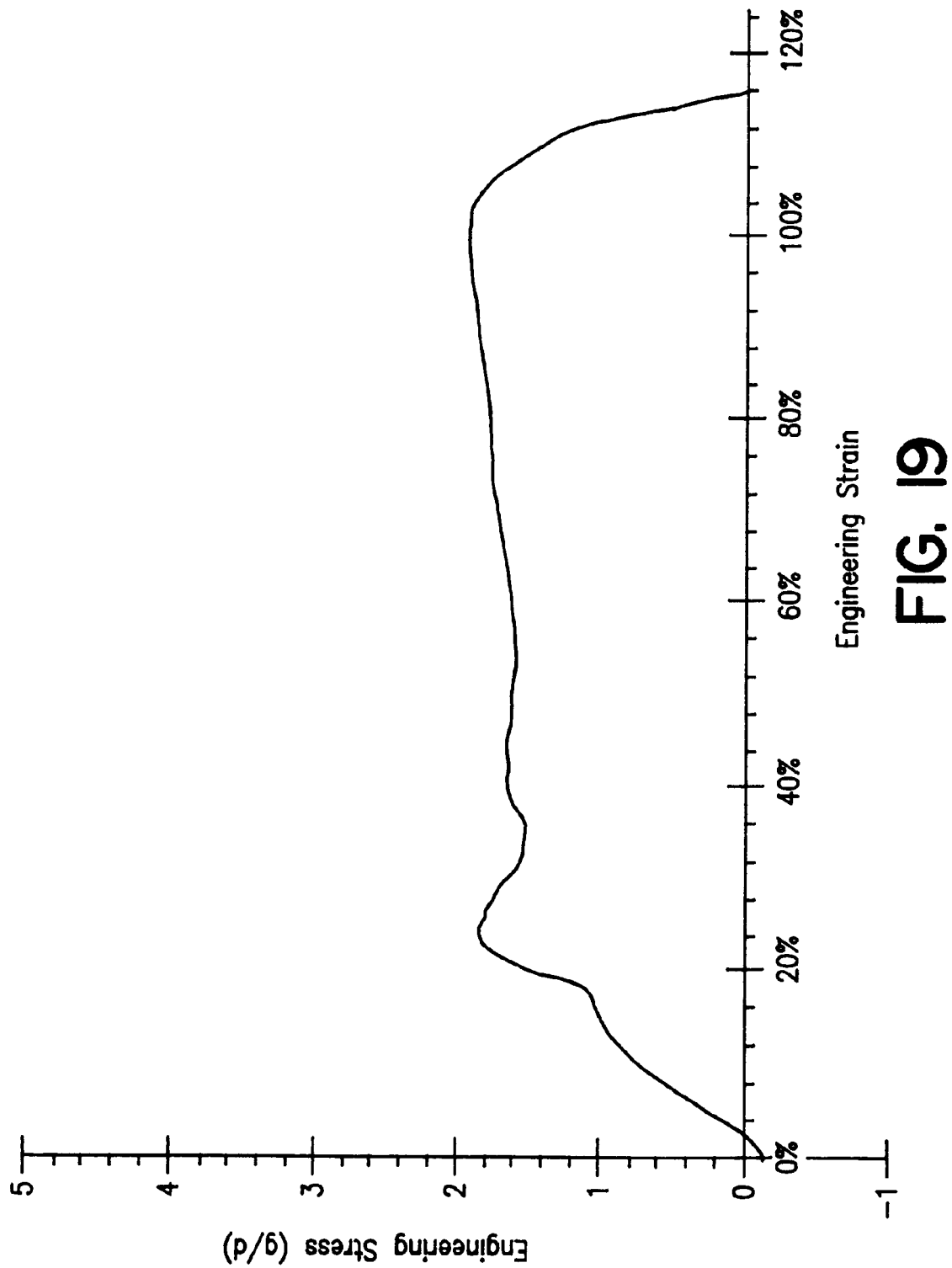
FIG. 19 is a graph illustrating the properties of a fiber using the process of the present invention with 41 percent overfeed.

A sample of PTFE fiber sold under the trademark GORE-TEX® with 7 twists per inch in the Z direction was obtained from W. L. Gore & Associates, Inc. This fiber was subjected to treatment according to the present invention with 41 percent overfeed, with the other conditions being the same as those in Example 1. After treatment, the denier of this fiber was measured to be 1830. The data from this Example are shown below in Table XVIII (the reported mean was calculated from the three successfully broken samples). The data are represented in graph form in FIG. 19.

TABLE XVIII

| Sample Number | Peak Engineering Stress (g/d) | Strain at Peak Engineering Stress (%) | Break Strain (%) | Toughness (g/d) |
|---|---|---|---|---|
| 1 | 2.15 | 11.5% | 60.4% | 0.916 |
| 2 | 2.26 | 90.9% | Did not Break* | |
| 3 | 2.26 | 91.0% | Did not Break* | |
| 4 | 1.88 | 96.4% | 116% | 1.696 |
| 5 | 1.86 | 23.2% | 117% | 1.710 |
| Mean | 2.08 | 62.6% | 97.9% | 1.441 |
| Stdev | 0.20 | 41.6% | 32.5% | 0.454 |
| CV | 9.42 | 66.4 | 33.18 | 31.5 |

*Did not break: End of stroke length reached, sample was still intact.

Example 13

Figure 20:
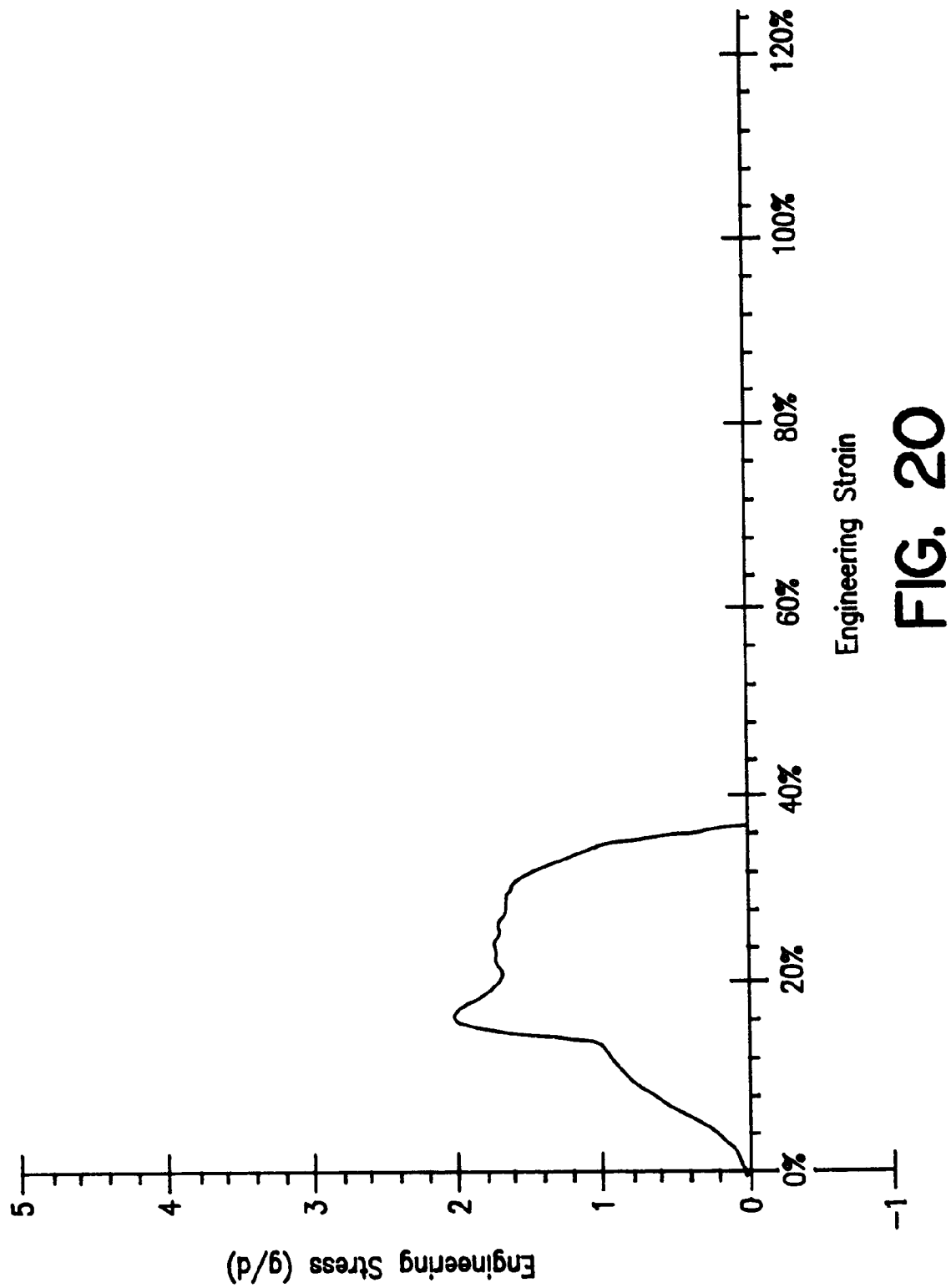
FIG. 20 is a graph illustrating the properties of a fiber using the process of the present invention with 68 percent overfeed.

A sample of PTFE fiber sold under the trademark GORE-TEX® with 7 twists per inch in the Z direction was obtained from W. L. Gore & Associates, Inc. This fiber was subjected to treatment according to the present invention with 68 percent overfeed, with the other conditions being the same as those in Example 1. After treatment, the denier of this fiber was measured to be 1900. The data from this Example are shown below in Table XIX (the reported mean was calculated from the two successfully broken samples). The data are represented in graph form in FIG. 20.

TABLE XIX

| Sample Number | Peak Engineering Stress (g/d) | Strain at Peak Engineering Stress (%) | Break Strain (%) | Toughness (g/d) |
|---|---|---|---|---|
| 1 | 1.74 | 25.1% | 61.6% | 0.647 |
| 2 | 2.02 | 90.8% | Did not Break* | |

TABLE XIX-continued

| Sample Number | Peak Engineering Stress (g/d) | Strain at Peak Engineering Stress (%) | Break Strain (%) | Toughness (g/d) |
|---|---|---|---|---|
| 3 | 1.99 | 16.7% | 36.8% | 0.428 |
| 4 | 2.02 | 90.8% | Did not Break* | |
| 5 | 1.76 | 125% | Did not Break* | |
| Mean | 1.91 | 69.9% | 49.2% | 0.537 |
| Stdev | 0.14 | 47.0% | 17.5% | 0.155 |
| CV | 7.55 | 67.3 | 35.7 | 28.8 |

*Did not break: End of stroke length reached, sample was still intact.

Considering Examples 7–13, the effects of varying rates of overfeed are shown In particular, it appears that desirable overfeed rates are up to about 70 percent. A preferred range for the overfeed rate is from about 10 percent to about 20 percent. Most preferred is an overfeed rate of about 15 percent. The fiber of all of these examples demonstrate improved toughness in comparison with the fiber of Comparative Example 1 and are thus likely to absorb more energy and perform better in applications demanding improved toughness.

Figure 26:
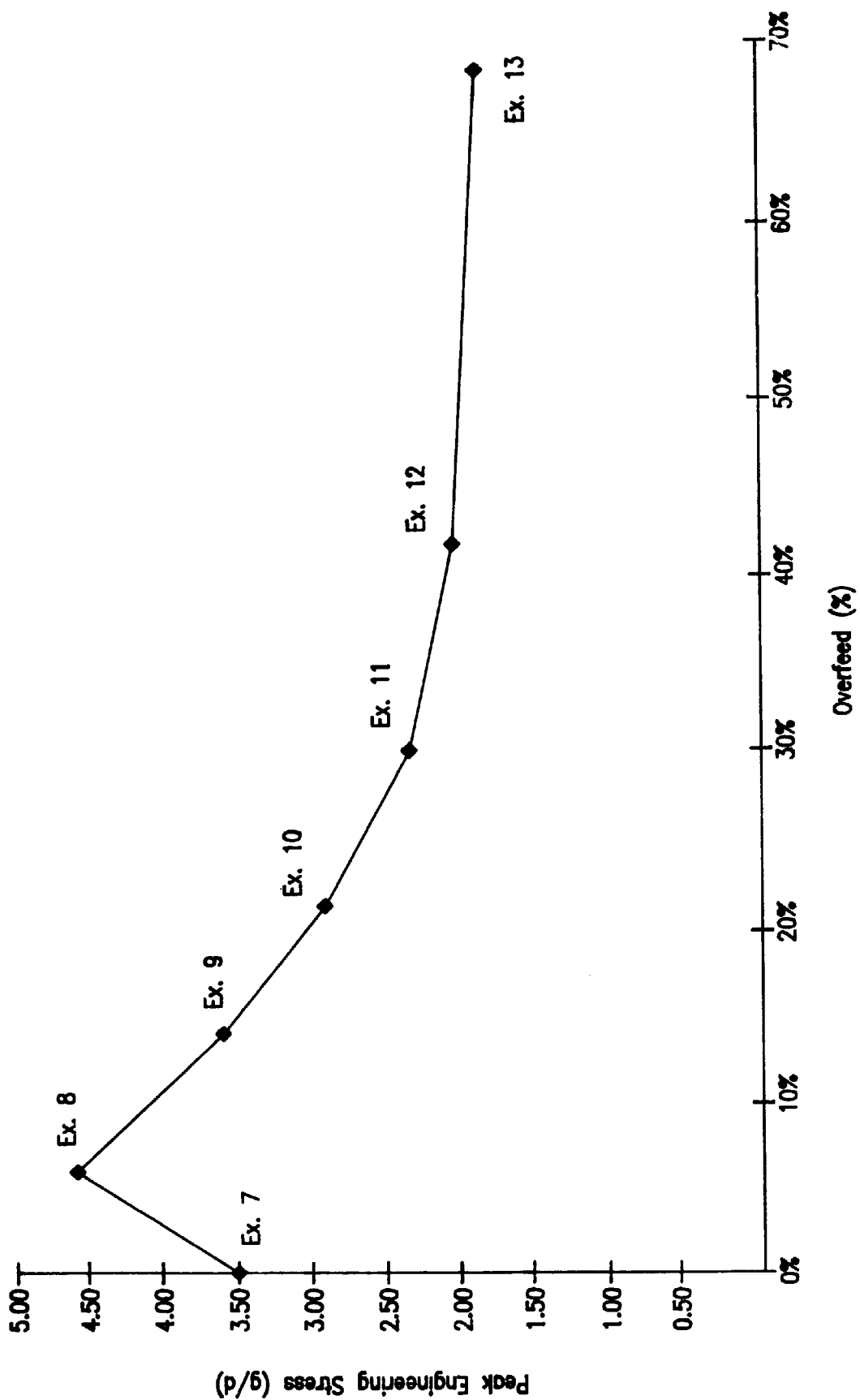
FIG. 26 is a graph illustrating the relationship in a fiber according to this invention of overfeed versus peak engineering stress.
Figure 27:
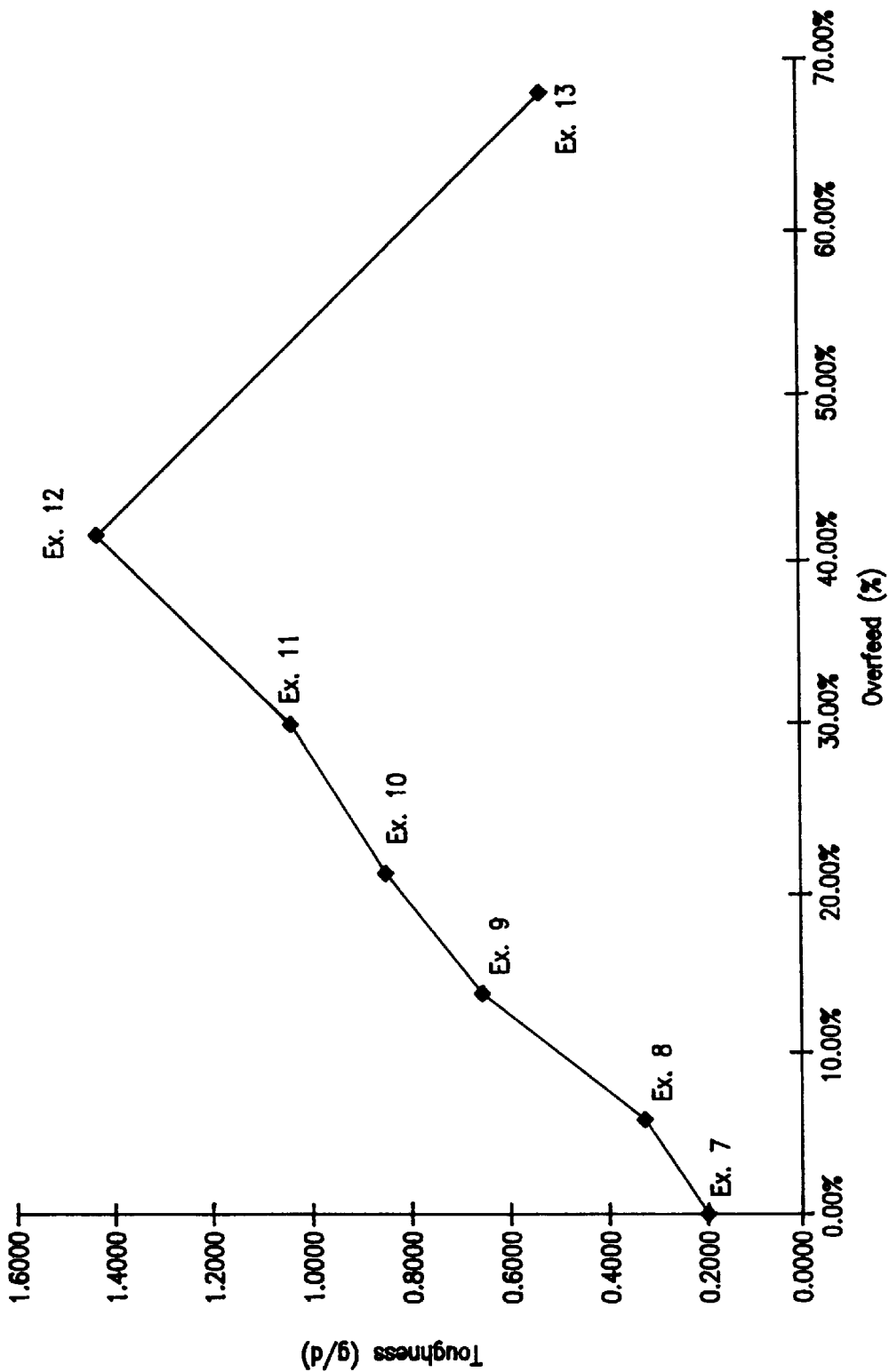
FIG. 27 is a graph illustrating the relationship in a fiber according to this invention of overfeed versus toughness.
Figure 28:
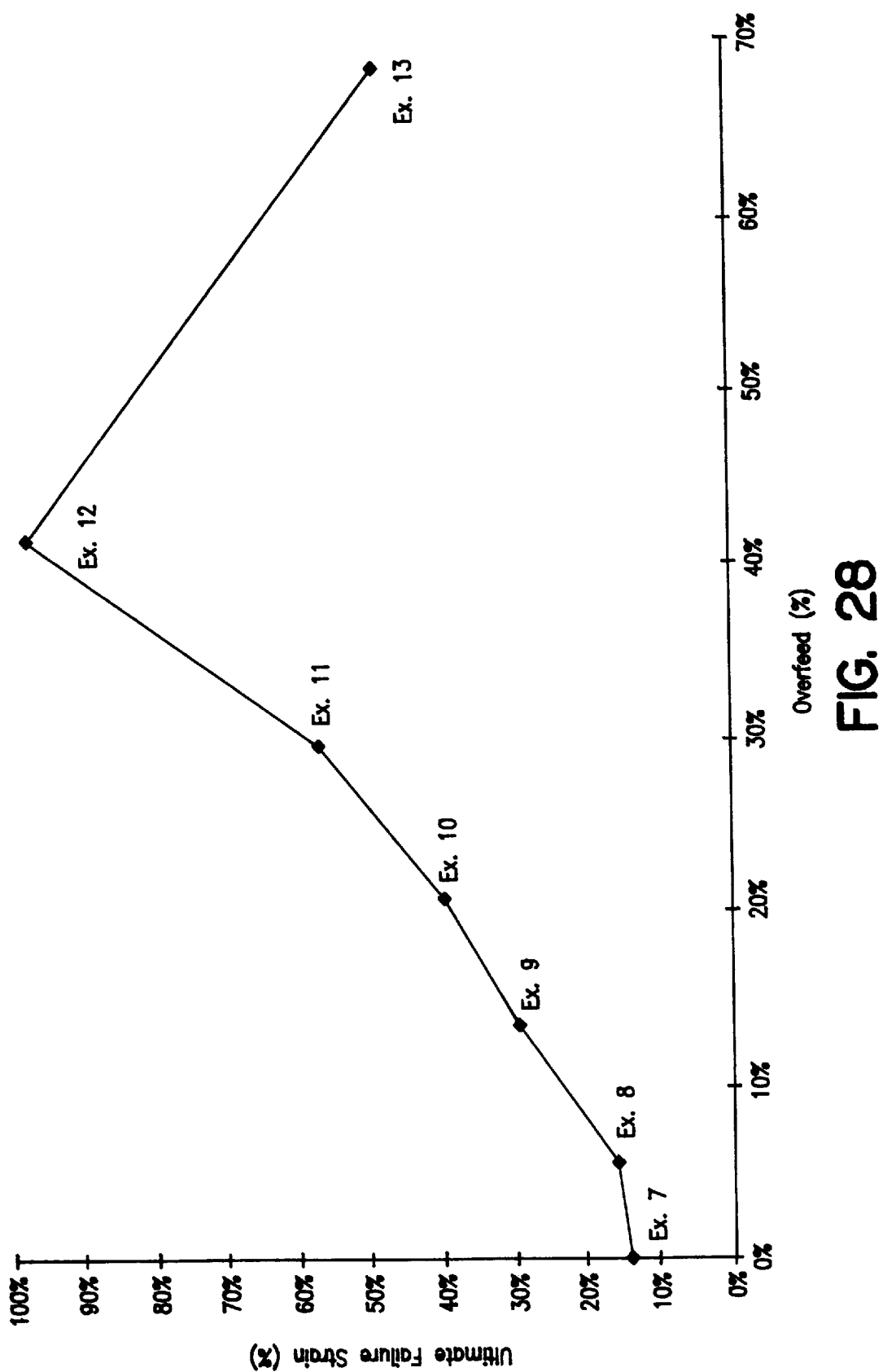
FIG. 28 is a graph illustrating the relationship in a fiber according to this invention of overfeed versus break strain.

The effect of overfeed on peak engineering stress for Examples 7–13 is shown in the graph of FIG. 26. The effect of overfeed on toughness for Examples 7–13 is shown in the graph of FIG. 27. The effect of overfeed on break strain for Examples 7–13 is shown in the graph of FIG. 28.

Examples Demonstrating the Effects of Varying Temperatures

Example 14

Figure 21:
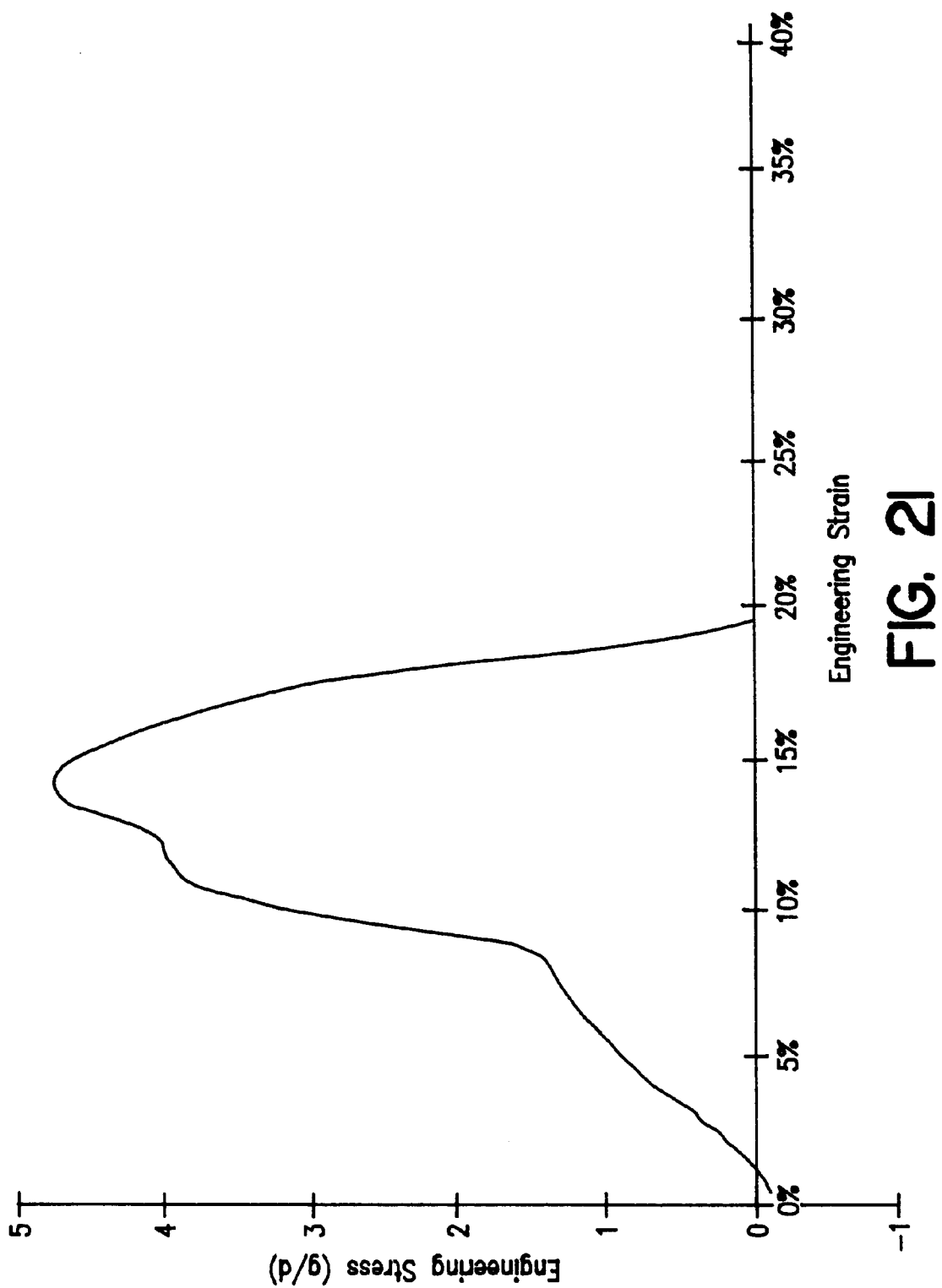
FIG. 21 is a graph illustrating the properties of a fiber after treatment according to the process of this invention at 350° C.

A sample of PTFE fiber sold under the trademark GORE-TEX® with 7 twists per inch in the z direction was obtained from W. L. Gore & Associates, Inc. The fiber was treated according to the process of this invention as described in Example 1 except that the temperature was 350° C. and the residence time was 60 seconds. After treatment, the denier of this fiber was measured to be 1260. The data generated for this fiber is shown below in Table XX. The data are presented graphically in FIG. 21.

TABLE XX

| Sample Number | Peak Engineering Stress (g/d) | Strain at Peak Engineering Stress (%) | Break Strain (%) | Toughness (g/d) |
|---|---|---|---|---|
| 1 | 4.97 | 13.7% | 19.4% | 0.431 |
| 2 | 4.23 | 13.0% | 18.7% | 0.367 |
| 3 | 4.42 | 13.0% | 18.2% | 0.373 |
| 4 | 4.73 | 14.2% | 19.5% | 0.432 |
| 5 | 4.80 | 12.4% | 19.3% | 0.442 |
| Mean | 4.63 | 13.3% | 19.0% | 0.409 |
| Stdev | 0.30 | 0.67% | 0.54% | 0.036 |
| CV | 6.52 | 5.04 | 2.82 | 8.70 |

Example 15

Figure 22:
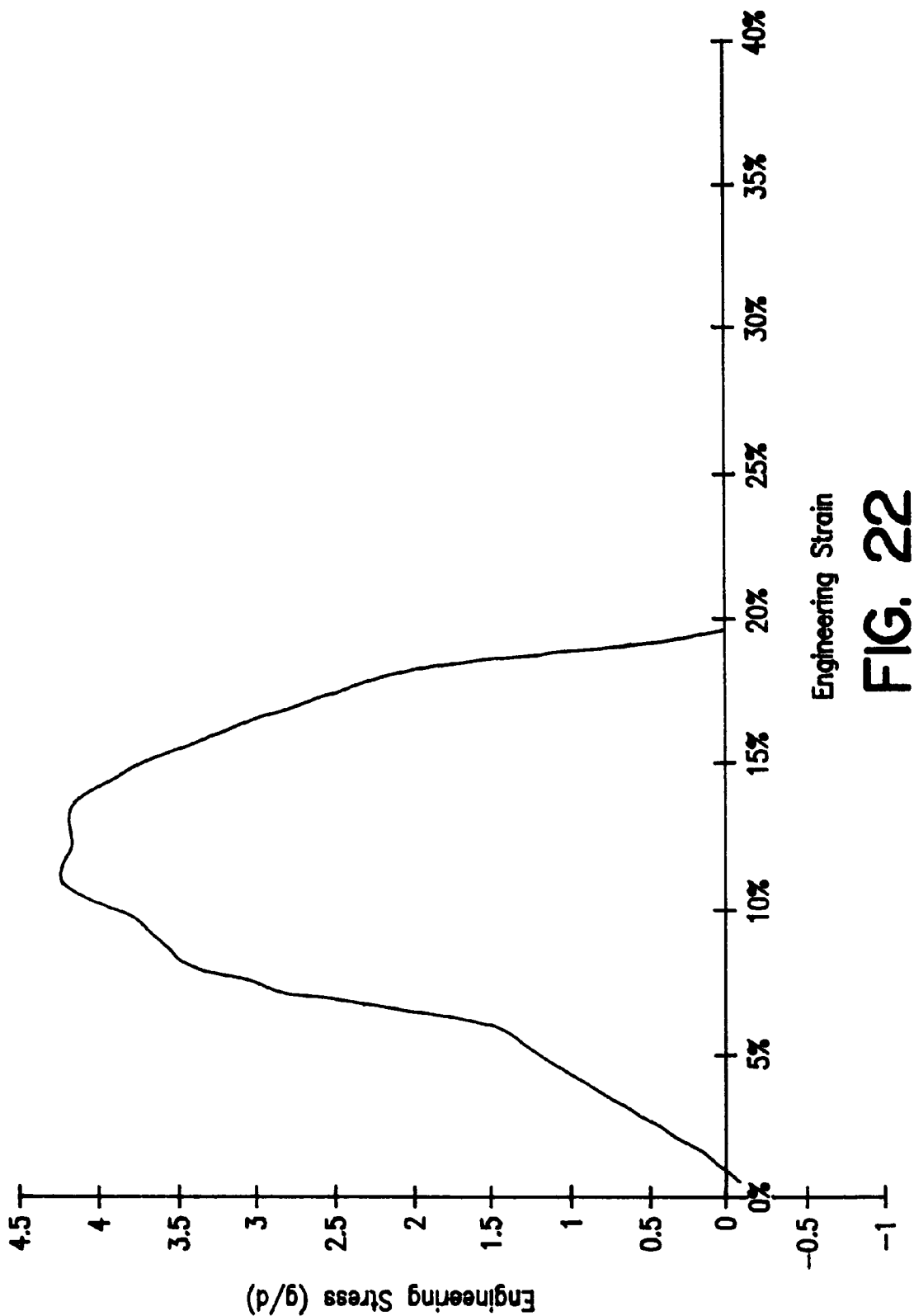
FIG. 22 is a graph illustrating the properties of a fiber after treatment according to the process of this invention at 375° C.

A sample of PTFE fiber sold under the trademark GORE-TEX® with 7 twists per inch in the z direction was obtained from W. L. Gore & Associates, Inc. The fiber was treated according to the process of this invention as described in Example 1 except that the temperature was 375° C. and the residence time was 60 seconds. After treatment, the denier of this fiber was measured to be 1280. The data generated for this fiber is shown below in Table XXI. The data are presented graphically in FIG. 22.

TABLE XXI

| Sample Number | Peak Engineering Stress (g/d) | Strain at Peak Engineering Stress (%) | Break Strain (%) | Toughness (g/d) |
|---|---|---|---|---|
| 1 | 4.15 | 12.8% | 21.2% | 0.510 |
| 2 | 4.08 | 11.4% | 19.3% | 0.443 |
| 3 | 3.96 | 11.8% | 19.8% | 0.453 |
| 4 | 4.13 | 11.3% | 19.3% | 0.455 |
| 5 | 4.13 | 10.9% | 18.6% | 0.435 |
| Mean | 4.09 | 11.6% | 19.6% | 0.459 |
| Stdev | 0.08 | 0.74% | 0.98% | 0.030 |
| CV | 1.88 | 6.35 | 5.00 | 6.45 |

Example 16

Figure 23:
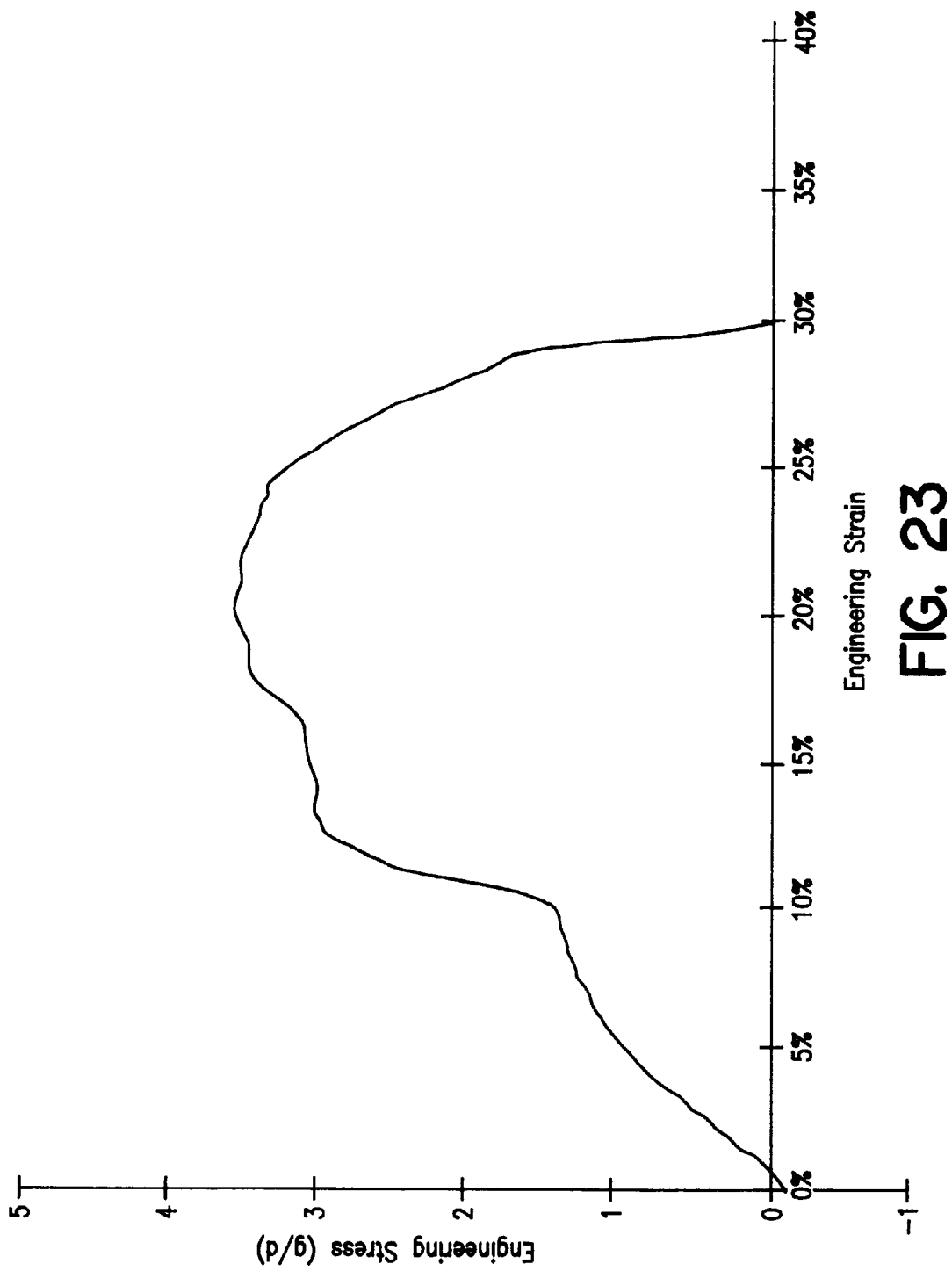
FIG. 23 is a graph illustrating the properties of a fiber after treatment according to the process of this invention at 400° C.

A sample of PTFE fiber sold under the trademark GORE-TEX® with 7 twists per inch in the z direction was obtained from W. L. Gore & Associates, Inc. The fiber was treated according to the process of this invention as described in Example 1. After treatment, the denier of this fiber was measured to be 1270. The data generated for this fiber is shown below in Table XXII. The data are presented graphically in FIG. 23.

TABLE XXII

| Sample Number | Peak Engineering Stress (g/d) | Strain at Peak Engineering Stress (%) | Break Strain (%) | Toughness (g/d) |
|---|---|---|---|---|
| 1 | 3.56 | 19.2% | 31.5% | 0.728 |
| 2 | 3.63 | 18.9% | 32.3% | 0.725 |
| 3 | 3.59 | 17.8% | 28.2% | 0.624 |
| 4 | 3.63 | 20.0% | 30.1% | 0.690 |
| 5 | 3.66 | 19.0% | 26.1% | 0.544 |
| Mean | 3.61 | 19.0% | 29.6% | 0.662 |
| Stdev | 0.04 | 0.81% | 2.53% | 0.078 |
| CV | 1.07 | 4.28 | 8.53 | 11.8 |

Example 17

Figure 24:
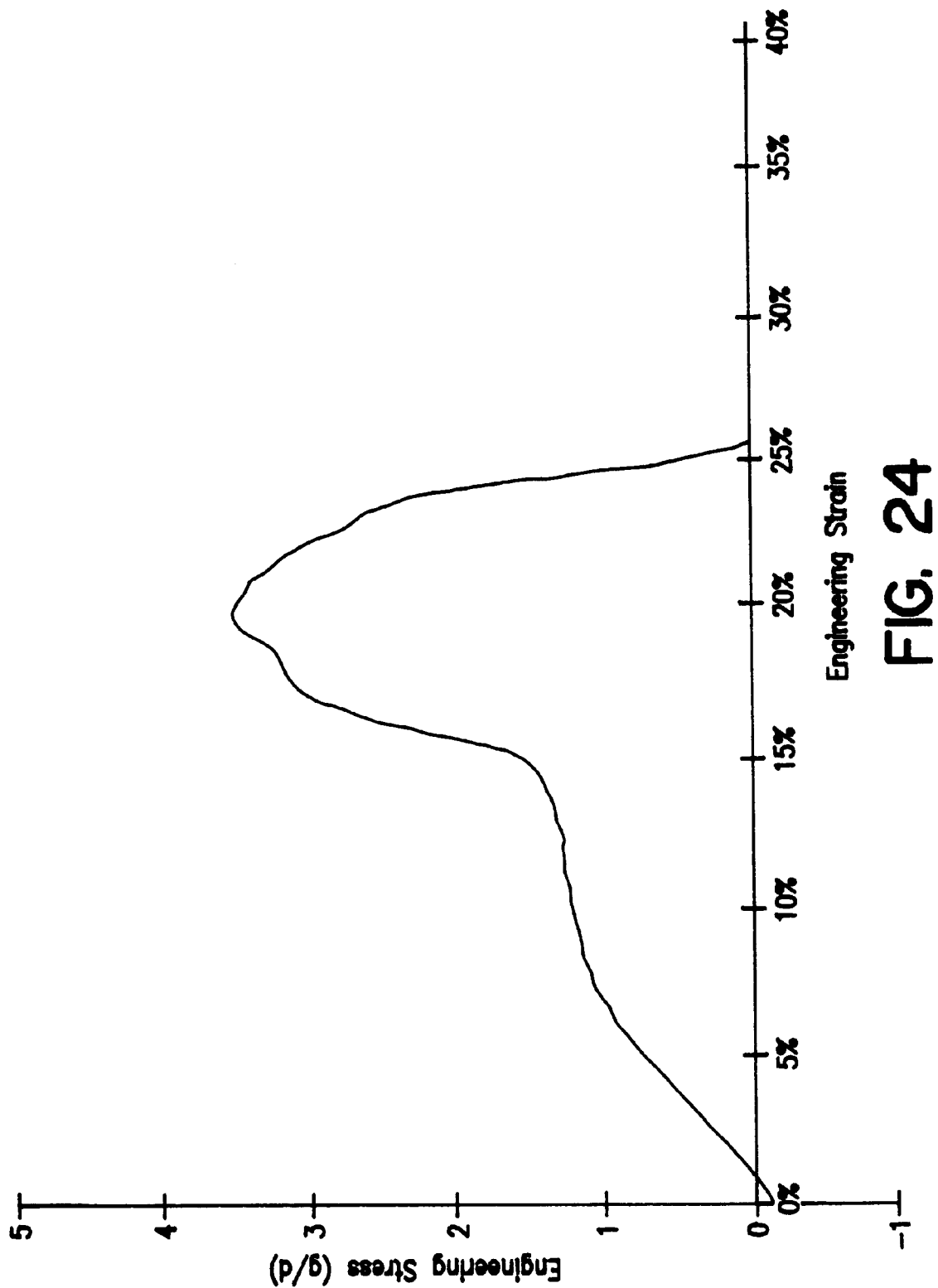
FIG. 24 is a graph illustrating the properties of a fiber after treatment according to the process of this invention at 475° C.

A sample of PTFE fiber sold under the trademark GORE-TEX® with 7 twists per inch in the z direction was obtained from W. L. Gore & Associates, Inc. The fiber was treated according to the process of this invention as described in Example 1 except that the temperature was 475° C. and the residence time was 2 seconds. After treatment, the denier of this fiber was measured to be 1250. The data generated for this fiber is shown below in Table XXIII. The data are presented graphically in FIG. 24.

TABLE XXIII

| Sample Number | Peak Engineering Stress (g/d) | Strain at Peak Engineering Stress (%) | Break Strain (%) | Toughness (g/d) |
|---|---|---|---|---|
| 1 | 3.26 | 17.1% | 23.2% | 0.340 |
| 2 | 3.54 | 20.1% | 25.7% | 0.415 |
| 3 | 3.19 | 17.8% | 23.8% | 0.345 |
| 4 | 3.80 | 23.1% | 30.9% | 0.629 |
| 5 | 2.15 | 18.5% | 22.7% | 0.268 |
| Mean | 3.18 | 19.3% | 25.3% | 0.399 |
| Stdev | 0.63 | 2.39% | 3.37% | 0.139 |
| CV | 19.8 | 12.4 | 13.3 | 34.8 |

Example 18

Figure 25:
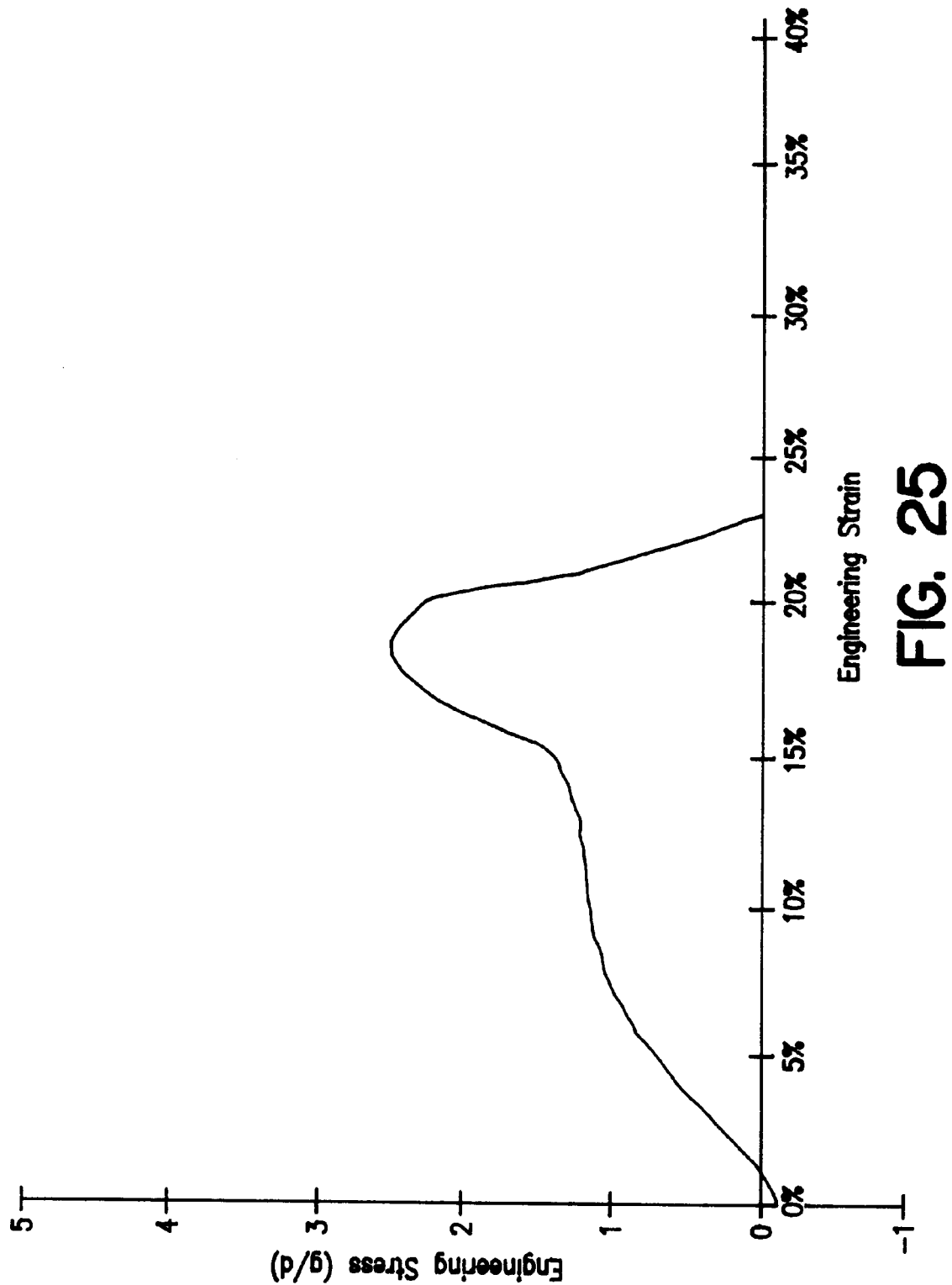
FIG. 25 is a graph illustrating the properties of a fiber after treatment according to the process of this invention at 475° C.

A sample of PTFE fiber sold under the trademark GORE-TEX® with 7 twists per inch in the z direction was obtained from W. L. Gore & Associates, Inc. The fiber was treated according to the process of this invention as described in Example 1 except that the temperature was 475° C. After treatment, the denier of this fiber was measured to be 1270. The data generated for this fiber is shown below in Table XXIV. The data are presented graphically in FIG. 25.

TABLE XXIV

| Sample Number | Peak Engineering Stress (g/d) | Strain at Peak Engineering Stress (%) | Break Strain (%) | Toughness (g/d) |
| --- | --- | --- | --- | --- |
| 1 | 1.51 | 17.4% | 21.3% | 0.202 |
| 2 | 2.50 | 18.6% | 22.8% | 0.261 |
| 3 | 1.68 | 19.4% | 23.1% | 0.232 |
| 4 | 2.72 | 17.1% | 21.3% | 0.262 |
| 5 | 2.67 | 18.3% | 22.9% | 0.269 |
| Mean | 2.22 | 18.28% | 22.3% | 0.245 |
| Stdev | 0.58 | 0.92% | 0.91% | 0.028 |
| CV | 26.1 | 5.08 | 4.10 | 11.4 |

Considering Examples 14–18, the effect of the temperature on the fiber according to this invention are shown. It appears that a desired temperature is from about 300° C. to about 500° C. A preferred range of the temperature is from about 350° C. to about 450° C. Most preferably, the temperature is about 400° C. One skilled in the art will understand how to vary temperature and take-up speed to obtain desired residence time. The fibers of all of these examples will demonstrate improved toughness in comparison with the fiber of Comparative Example 1.

Examples Showing Improvements in Dental Floss

Comparative Example 9

Figure 29:
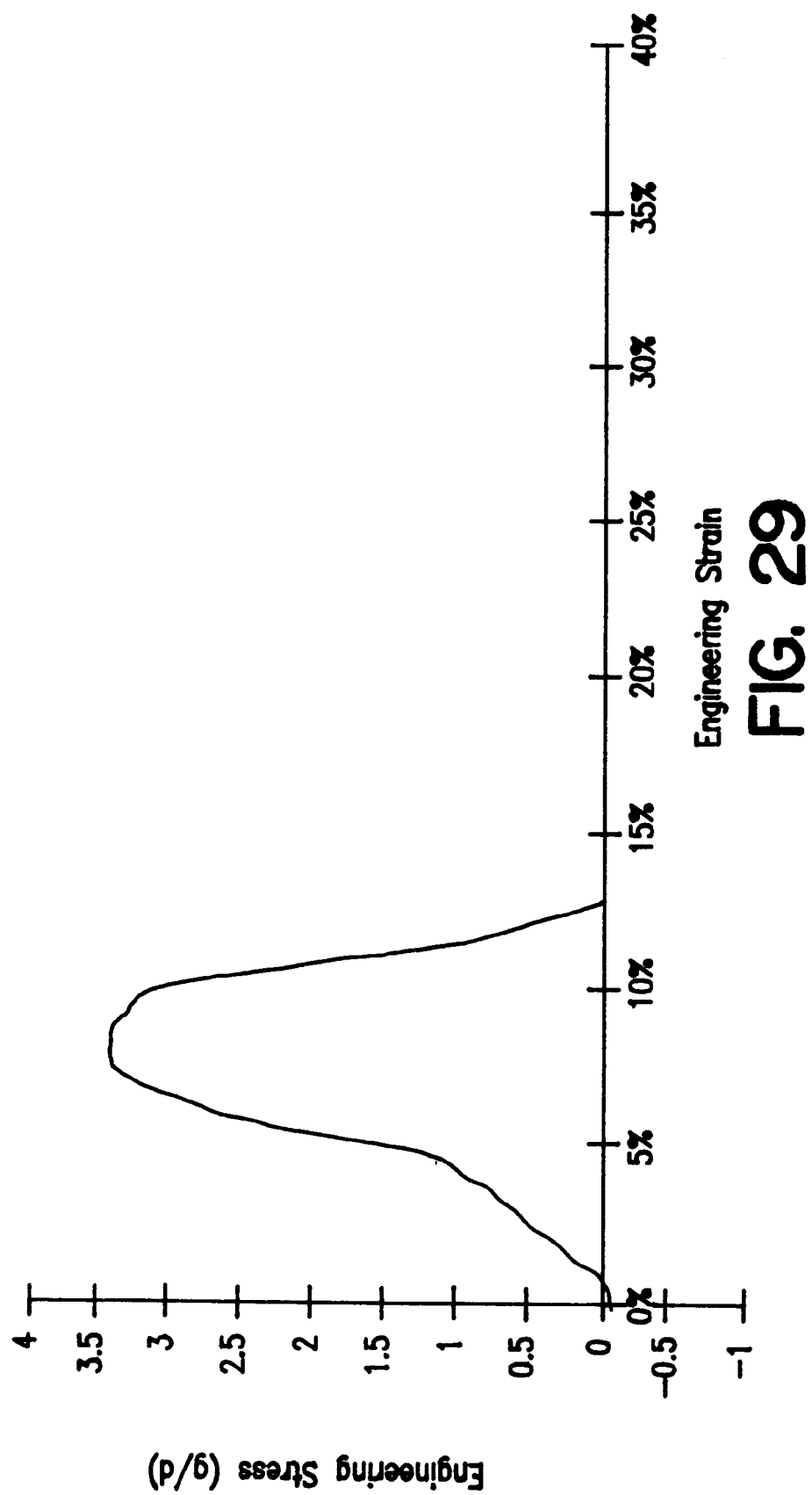
FIG. 29 is a graph illustrating the properties of dental floss before treatment with the process of this invention.

A sample of unwaxed dental floss was produced in accordance with Example 1 of the disclosure in U.S. Pat. No. 5,518,012. The dental floss was measured to be 1170 denier, having a width of 1.1 mm and a thickness of 76 μm. Five samples of this fiber were tested in the same manner and for the same properties as in Comparative Example 1 hereof. The results are presented in Table XXV below. The data are presented graphically in FIG. 29.

TABLE XXV

| Sample Number | Peak Engineering Stress (g/d) | Strain at Peak Engineering Stress (%) | Break Strain (%) | Toughness (g/d) |
| --- | --- | --- | --- | --- |
| 1 | 4.69 | 7.52% | 12.4% | 0.275 |
| 2 | 2.44 | 7.76% | 12.4% | 0.165 |
| 3 | 1.87 | 8.93% | 12.8% | 0.141 |
| 4 | 3.65 | 7.89% | 12.1% | 0.210 |
| 5 | 3.37 | 7.44% | 12.5% | 0.207 |
| Mean | 3.20 | 7.91% | 12.4% | 0.200 |
| Stdev | 1.09 | 0.60% | 0.25% | 0.051 |
| CV | 34.1 | 7.57 | 1.98 | 25.8 |

Example 19

Figure 30:
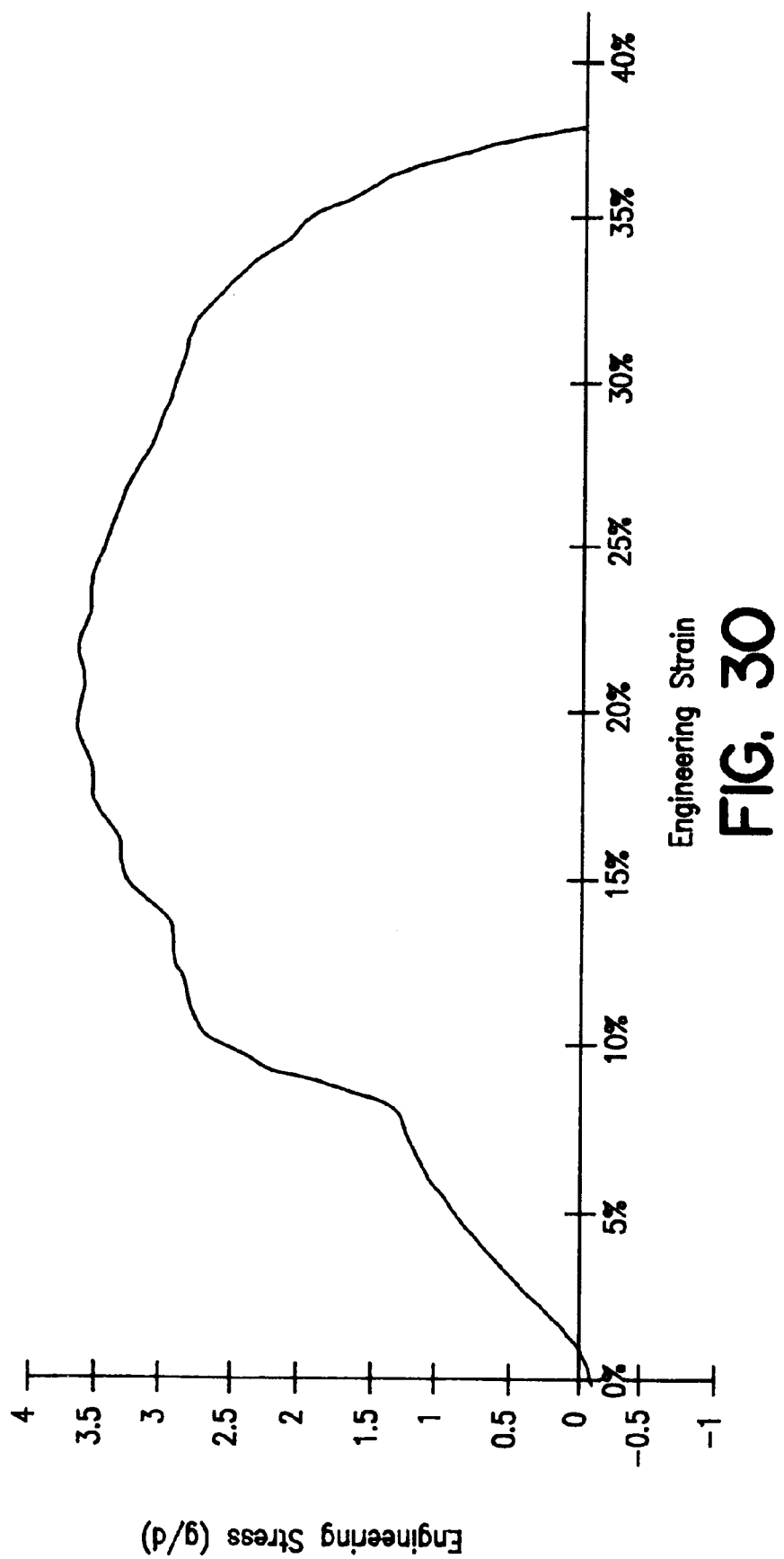
FIG. 30 is a graph illustrating the properties of dental floss after treatment with the process of this invention.

The dental floss of Comparative Example 9 was treated by the process of this invention using the same conditions as defined in Example 1. After treatment, the denier of this fiber was measured to be 1430. The same tests were also performed and the results are presented below in Table XXVI. This data indicates dramatic improvements over the dental floss of Comparative Example 9 in the strain at peak engineering stress, the break strain, and the toughness of the fiber after treatment according to the inventive process. The properties shown in Table XXVI indicate that the treated fiber will perform well as a dental floss. Specifically, the fiber of this Example 19 will likely perform better as a dental floss (including being less likely to break) than the fiber of Comparative Example 9 because of the enhanced properties of the fiber of Example 19. The data are presented graphically in FIG. 30.

TABLE XXVI

| Sample Number | Peak Engineering Stress (g/d) | Strain at Peak Engineering Stress (%) | Break Strain (%) | Toughness (g/d) |
| --- | --- | --- | --- | --- |
| 1 | 3.67 | 18.9% | 29.0% | 0.654 |
| 2 | 3.73 | 20.0% | 50.1% | 1.226 |
| 3 | 3.65 | 19.6% | 37.7% | 0.918 |
| 4 | 3.46 | 17.8% | 23.8% | 0.449 |
| 5 | 3.56 | 19.3% | 25.6% | 0.536 |
| Mean | 3.61 | 19.1% | 33.3% | 0.757 |
| Stdev | 0.11 | 0.85% | 10.9% | 0.316 |
| CV | 2.96 | 4.44 | 32.6 | 41.8 |

The examples presented herein demonstrate the range of the desired properties for the inventive fiber depending upon the process parameters used to produce the fiber. One skilled in the art will understand that these properties may be manipulated and optimized as necessary for any particular application by manipulating and optimizing the process parameters disclosed herein.

Using the method of this invention, PTFE fiber can be produced that withstands far greater sewing speeds. This increases productivity and efficiencies in sewing and has many other inherent advantages. The increased toughness of the PTFE fibers also provides advantages in other applications mentioned herein and as will be recognized by those skilled in the art from this disclosure.

Although described in connection with specific examples, the present invention is not intended to be limited thereto, but rather includes such modifications and variations as are within the scope of the appended claims.

What is claimed is:

1. A fiber comprising polytetrafluoroethylene (PTFE), wherein said fiber has a toughness greater than about 0.36 g/d, and a break strain greater than 15.5%.

2. A fiber as defined in claim 1, wherein said toughness is between 0.36 and 1.01 g/d.

3. A fiber as defined in claim 1, wherein said toughness is between 0.50 and 0.80 g/d.

4. A fiber as defined in claim 1, wherein said toughness is about 0.60 g/d.

5. A fiber as defined in claim 1, wherein said break strain is greater than 20%.

6. A fiber as defined in claim 1, wherein said break strain is greater than 25%.

7. A fiber as defined in claim 1, wherein said break strain is greater than 30%.

8. A fiber as defined in claim 1, wherein said break strain is greater than 35%.

9. A fiber as defined in claim 1, wherein said toughness is between 0.36 and 1.01 g/d and said break strain is greater than 25%.

10. A fiber as defined in claim 1, wherein said toughness is between 0.50 and 0.80 g/d and said break strain is greater than 30%.

11. A fiber as defined in claim 1, wherein said toughness is about 0.65 g/d and said break strain is about 30%.

12. A fiber as defined in claim 1, wherein said fiber has a peak engineering stress greater than 1.6 g/d.

13. A fiber as defined in claim 12, wherein said peak engineering stress is greater than 2.0 g/d.

14. A fiber as defined in claim 12, wherein said peak engineering stress is greater than 2.5 g/d.

15. A fiber as defined in claim 12, wherein said peak engineering stress is greater than 3.0 g/d.

16. A fiber as defined in claim 12, wherein said peak engineering stress is between 3.0 and 5.0 g/d.

17. A fiber as defined in claim 11, wherein said peak engineering stress is about 3.7 g/d.

18. A fiber as defined in claim 1 used as a dental floss.

19. A fiber as defined in claim 1 further comprising at least one pigment.

* * * * *